(12) United States Patent
Yang et al.

(10) Patent No.: US 7,902,303 B2
(45) Date of Patent: Mar. 8, 2011

(54) ALIPHATIC POLYESTER POLYMER COMPOSITIONS AND PREPARATION METHOD THEREOF

(75) Inventors: Jean-Dean Yang, Taoyuan (TW); Jui-Hsiang Chen, Hsinchu (TW); Meng-Yow Hsieh, Taipei (TW); Pei Pei Cheng, Taoyuan County (TW)

(73) Assignee: Industrial Technology Research Institute, Hsinchu (TW)

( * ) Notice: Subject to any disclaimer, the term of this patent is extended or adjusted under 35 U.S.C. 154(b) by 285 days.

(21) Appl. No.: 11/606,918

(22) Filed: Dec. 1, 2006

(65) Prior Publication Data

US 2007/0155943 A1 Jul. 5, 2007

(51) Int. Cl.
*A61F 2/04* (2006.01)
*C08L 67/04* (2006.01)

(52) U.S. Cl. .......... 525/450; 424/426; 606/908; 606/910

(58) Field of Classification Search .................. 525/444; 606/908, 910
See application file for complete search history.

(56) References Cited

U.S. PATENT DOCUMENTS

| | | | |
|---|---|---|---|
| 4,080,318 A | | 3/1978 | Smith et al. |
| 4,674,488 A | * | 6/1987 | Nashef et al. .................. 606/76 |
| 4,883,618 A | * | 11/1989 | Barrows .......................... 264/49 |
| 5,147,897 A | | 9/1992 | Morimoto et al. |
| 5,218,073 A | * | 6/1993 | Evans .............................. 528/73 |
| 5,270,400 A | | 12/1993 | Spinu |
| 5,412,005 A | | 5/1995 | Bastioli et al. |
| 5,470,944 A | * | 11/1995 | Bonsignore ................... 528/354 |
| 5,665,831 A | | 9/1997 | Neuenschwander et al. |
| 5,716,981 A | * | 2/1998 | Hunter et al. .................. 514/449 |
| 6,211,249 B1 | | 4/2001 | Cohn et al. |
| 6,476,156 B1 | | 11/2002 | Kim et al. |
| 6,488,938 B1 | * | 12/2002 | Ogura et al. ................... 424/400 |
| 6,770,717 B2 | | 8/2004 | Kim et al. |
| 6,818,675 B2 | * | 11/2004 | El Ghobary et al. .......... 521/129 |
| 2002/0183856 A1 | * | 12/2002 | Yamauchi et al. .......... 623/23.72 |
| 2006/0047088 A1 | | 3/2006 | Yamane et al. |

FOREIGN PATENT DOCUMENTS

| | | |
|---|---|---|
| EP | 1025870 A1 | 8/2000 |
| EP | 1741456 A1 | 1/2007 |
| JP | 06313063 A * | 11/1994 |
| WO | WO-96/01863 A1 | 1/1996 |
| WO | WO-96/31552 A1 | 10/1996 |
| WO | WO-99/28367 A1 | 6/1999 |
| WO | WO-2005/059003 A1 | 6/2005 |

OTHER PUBLICATIONS

Meek et al., Microsurgery, 1999, vol. 19, pp. 381-388 (XP-002457422).
Luis et al., Microsurgery, 2007, vol. 27, pp. 125-137 (XP-002457423).
Dunnen et al., Journal of Biomedical Materials Research, 2000, vol. 51, pp. 575-585. (XP-002457424).
Pulkkinen et al., European Journal of Pharmaceutical Sciences, 2007, vol. 31, pp. 119-128.
Zhao et al., Journal of Applied Polymer Science, 2004, vol. 92, pp. 3333-3337 (XP-002457425).
Lai et al., Reactive & Functional Polymers, 2005, vol. 65 No. 3, pp. 309-315. (XP-005181927).
Lietz et al., Biotechnology and Bioengineering, 2006, vol. 93 No. 3, pp. 99-109 (XP-003005189).
Tserki et al., Polymer Degradation and Stability, 2006, vol. 91, pp. 367-376.
Kylma et al., Polymer, 2001, vol. 42, pp. 3333-3343 (XP-004313874).
Woo et al., Polymer Bulletin, 1995, vol. 35 No. 4, pp. 415-421 (XP-00005245500).
Zhong et al., Journal of Applied Polymer Science, 1999, vol. 74 No. 10, pp. 2546-2551 (XP-002413318).
Yong et al., Database Compendex/EL (Online) Engineering Information, Inc., Database accession No. E2006199868839 (XP-002457426) & E2006159817248 (XP-002457427).
Tserki et al., Polymer Degradation and Stability, 2006, vol. 377-384 (XP-005169560).
Lee et al. (Journal of Control Release, vol. 73, pp. 315-327, 2001).
Cohn et al. (Biomaterials, vol. 26, pp. 2297-2305, 2005).

* cited by examiner

*Primary Examiner* — Robert Sellers
(74) *Attorney, Agent, or Firm* — Birch, Stewart, Kolasch & Birch, LLP

(57) ABSTRACT

An aliphatic polyester polymer compositions and preparation method thereof. The invention provides a bioresorbable aliphatic polyester copolymer, comprising the reaction product of a first polyester, a second polyester, and a coupling agent. Specifically, the first polyester and second polyester have the same repeat units, but different weight average molecular weights. Methods for preparing the aliphatic polyester copolymer are provided, in which the first polyester reacts with the second polyester in the presence of the coupling agent, undergoing copolymerization.

35 Claims, 16 Drawing Sheets
(7 of 16 Drawing Sheet(s) Filed in Color)

ALIPHATIC POLYESTER POLYMER COMPOSITIONS AND PREPARATION METHOD THEREOF

BACKGROUND OF THE INVENTION

1. Field of the Invention

The invention relates to polyester copolymers, and more particularly to a bioresorbable aliphatic polyester copolymer with superior mechanical properties and modifiable decomposition period.

2. Description of the Related Art

Recently, with increased maturity of polymer technologies, polymer applications are involved in not only traditional plastics and synthetic resin industries but also high technology industries such as livelihood, and biotechnology. Some relative polymer materials with specific properties are critical for the related industries. For example, bioresorbable polymer, particularly those that include synthetic polymers or a combination of synthetic and naturally occurring polymers, have been used in a variety of medical and environmental protection applications.

Naturally occurring bioresorbable polymers include polypeptides (such as collagen and gelatin), polyamino acids (such as poly-L-glutamic acid and poly-L-lysine) and polysaccharides (such as hyaluronic acid, alginic acid, chitin, and chitosan). Naturally occurring bioresorbable polymers, however, have poor mechanical properties and are difficult to process and mass-produce.

Accordingly, attention has turned to synthetic polymers. Bioresorbable synthetic polymers commonly and currently used include polycaprolactone (PCL), polylatic acid (PLA), polyglycolic acid (PGA), poly lactide-co-glycolide (PLGA)), polyvinyl alcohol (PVA), polyhydroxy butyrate (PHB), polyanhydride, and polyortho ester. Since the aforementioned synthetic polymers mostly comprise a hydrolysable functional group, such as the ester group, the polymers hydrolyze gradually, and are thereby suitable for wide use in medical and environmental protection applications.

In some clinical conditions, implant fixation devices or materials are employed to fix soft or hard tissues. The fixation devices or materials must be removed from the host by a second procedure to avoid rejection, if they cannot biodegrade or be bioresorbed. The second procedure, however, is not only intrusive but also increases risk of infection and complications. Thus, bioresorbable fixation devices or materials have been widely developed and used in medical appli- Smith et al. in U.S. Pat. No. 4,080,318 disclose a polycaprolactone urethane derivative, comprising the reaction product of polycaprolactone polyol and polycarboxylic acid anhydride via copolymerization, wherein the polycaprolactone polyol has a molecular weight of between 290 to 6000, a hydroxyl functionality between 15 to 600, and at least one carboxylic anhydride group. Specifically, the polycaprolactone urethane derivative can present a cross-linking configuration.

Bastioli et al. in U.S. Pat. No. 5,412,005 discloses a bioresorbable polymer composition that contains a starch-based component and a polymeric component. The polymeric component comprises polymer of hydroxyacids or mixtures thereof with polymers derived from ethylenically unsaturated monomers, such as PVA and EVA.

Neuenschwander et al in U.S. Pat. No. 5,665,831 disclose biocompatible block copolymers containing two distinct copolymer blocks. The block copolymers comprise the reaction product of α,ω-dihydroxypolyesters acid (or 3-hydroxyvaleric acid reacted) with ethylene glycol, or α,ω-dihydroxypolyesters with diisocyanate, diacid hilide, or phosgene. The biocompatible block copolymers exhibit bioresorbable properties and are suitable for implant materials.

Cohn et al. in U.S. Pat. No. 6,211,249 disclose an AB diblock comprising polyester polyether block copolymers, in which A block is derived from a polyester monomer, and B block is a polyalkylene oxide moiety with terminal non-reactive functional groups such as alkyl aryl, or aralkyl. The polyester polyether block copolymer has been applied to surgical operation to prevent adhesion.

Young Ha Kim in U.S. Pat. No. 6,476,156 discloses a process for preparing a bioresorbable triblock copolymer, comprising polyethyleneglycol/polylactide (or polyglycolide or polycaprolactone)/polyethyleneglycol triblock copolymers. The process thereof comprises the step of synthesizing a polylactide (or polyglycolide or polycaprolactone) having hydroxy groups at both ends, and a step of coupling the polylactide with polyethyleneglycol having acylhalide group of a high reactivity at one of its ends. Due to superior biocompatibility, the triblock copolymer is suitable for serving as a biomaterial for tissue engineering or as a polymeric carrier for drug release.

Kim et al. in U.S. Pat. No. 6,770,717 disclose a sequentially ordered bioresorbable lactide (or glycolide or lactide/glycolide)/epsilon-caprolactone multi-block copolymer having proper degradation properties and enhanced mechanical properties such as flexibility and elasticity.

Lee et al. (journal of control release, vol. 73, 315-327, 2001) disclose a process for preparing polyethyleneglycol/polycaprolactone diblock copolymer, with hexamethylene diisocyanate (HDI) as a coupling agent.

Cohn et al. (Biomaterials, 26, p. 2297-2305, 2005) disclose a triblock copolymer with a PLA-PCL-PLA structure (PLA: poly L-lactide; PCL: polycaprolactone), exhibiting superior flexibility. Specifically, the mechanical strength of the triblock copolymer can be adjusted by modifying the molecular weight of PLA.

The biodegradation period and mechanical properties of a bioresorbable polymer are key features in its utilization. There is still a need to develop a novel bioresorbable polymer with superior mechanical properties and modifiable biodegradation period.

The above references do not disclose or teach how to improve the mechanical strength and biodegradability of the polyester material. For example, due to the long biodegradation period of more than three years, the application of the polycaprolactone has been limited. Moreover, conventional polyester materials have high stiffness and are not suitable to serve as implant fixation devices used in human body. Therefore, the embodiments of the invention provided biodegradable materials by copolymerizing polyesters with different molecular weight. The obtained polyester polymer has modifiable biodegradation period and sufficient flexibility and elasticity.

BRIEF SUMMARY OF THE INVENTION

The invention provides an aliphatic polyester copolymer, comprising the reaction product a first polyester, a second polyester, and a coupling agent. Specifically, the first polyester and second polyester have the same repeat units, but different molecular weights. In the invention, the reactants can further comprise a catalyst.

Methods for preparing an aliphatic polyester copolymer are provided, in which the first polyester reacts with the second polyester in the presence of the coupling agent, undergoing copolymerization.

The invention further provides an implantable medical device or material, comprising an aliphatic polyester copolymer. According to the invention, the implantable device can function for nerve repair, dura mater repair, ligament repair, tendon repair, hernia repair, rotator cuff repair, meniscal repair, muscle repair, sling, joint repair, spinal repair, craniofacial repair, and maxiofacial repair. Specifically, the implantable device can serve as a medical device for repairing hard or soft tissues.

A detailed description is given in the following with reference to the accompanying drawing.

BRIEF DESCRIPTION OF THE DRAWINGS

The patent or application file contains at least one drawing executed in color. Copies of this patent or patent application publication with color drawing(s) will be provided by the office upon request and payment of the necessary fee.

The invention can be more fully understood by reading the subsequent detailed description and examples with references made to the accompanying drawings, wherein.

DETAILED DESCRIPTION OF THE INVENTION

Figure 1:
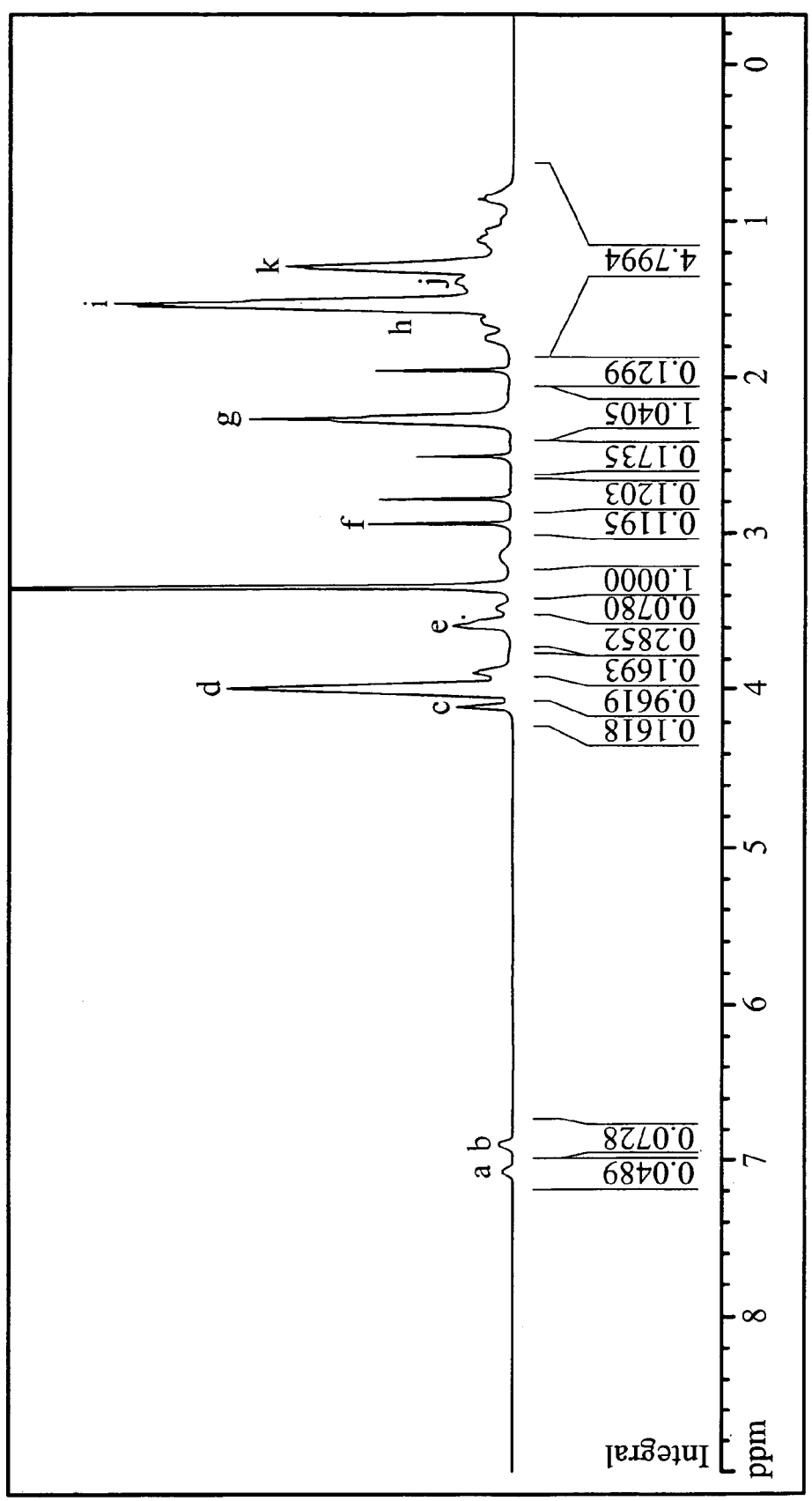
FIG. 1 shows the $^1$H-NMR spectrum of the aliphatic polyester copolymer of Example 1.

In the degradation of bioresorbable polyester, the ester bonds in the amorphous region are first subjected to hydrolysis, and then the water molecules hydrolyzes the ester bonds in the crystalline region. In general, conventional polyester materials exhibit higher crystallinity and have long biodegradation period. In the embodiment of the invention, an aliphatic coupling agent (such as $H_{12}MDI$) is used to copolymerize the polyester with different molecular weight, thereby reducing the crystallinity thereof. Since the obtained urethane linkage reduces the crystallinity, the biodegradation period of the aliphatic polyester polymer compositions according to the invention can be modifiable The following description is the best-contemplated mode of carrying out the invention. This description is made for the purpose of illustrating the general principles of the invention and should not be taken in a limiting sense. The scope of the invention is best determined by reference to the appended claims.

The invention provides a novel bioresorbable aliphatic polyester copolymer. The bioresorbable aliphatic polyester copolymer is prepared by copolymerizing first and second polyesters, which have the same repeat units but different molecular weights, in the presence of a coupling agent, having advantages of easy preparation and availability in great quantity. Further, the mechanical properties and biodegradation period thereof can be optionally adjusted by modifying the difference of the molecular weights and the weight ratio, between the first polyester and the second polyester.

The first and second polyesters can be derived from the same repeat unit, and have a hydroxyl functionality not less than 2. The repeat unit of polyester is synthesized from monomers of -caprolactone, -butyrolactone, L-lactide, D-lactide, D, L-lactide, L-lactic acid, D-lactic acid, D, L-lactic acid, glycolide, glycolic acid, -hydroxy hexonoic acid, -hydroxy butyric acid, -valerolactone, -hydroxy valeric acid, hydroxybutyric acids, malic acid, or copolymers thereof. When the polyester has a hydroxyl functionality of 2, the obtained aliphatic polyester copolymer is a linear copolymer. Furthermore, when the polyester has a hydroxyl functionality of more than 2, the obtained aliphatic polyester copolymer is a network copolymer.

The weight average molecular weights of the first and second polyesters are between 150~50000 daltons, preferably 200~30000 daltons, more preferably 200~20000 daltons. The weight ration between the first and second polyesters can be 9.5:0.5~0.5:9.5, preferably 8:2~2:8, more preferably 7:3~3:7. Specifically, the mechanical strength of the bioresorbable aliphatic polyester copolymer is improved when the polyester, having higher weight average molecular weights, is present in a higher weight ratio.

According to the invention, the biodegradation period of the aliphatic polyester copolymer is also adjustable by modifying the difference of the weight average molecular weights between the first polyester and the second polyester, which can be of more than 200 daltons, preferably 500 daltons. Specifically, the biodegradation period of the aliphatic polyester copolymer can be optionally adjusted by modifying the difference of the weight average molecular weights between the first polyester and the second polyester, and 1~36 months or less than 36 months. For example, the biodegradation period of the aliphatic polyester copolymers can be 1~12 months for short-term implantation, and 13~36 months for long-term implantation.

The coupling agent of the invention must have a functionality not less than 2, and can react with the hydroxyl group of the first and second polyester, performing a coupling reaction. The functional group of the coupling agent can be epoxy group, anhydride group, or isocyanate group. The coupling agent can be aliphatic isocyanate compounds having 2 or more —N=C=O groups, such as methylene-bis-(4-cyclohexyl diisocyanate) ($H_{12}MDI$), 1,6-Diisocyanatohexane (HDD, 5-isocyanato-1-(isocyanatomethyl)-1,3,3-trimethylcyclohexane (IPDI), tetramethyl-m-xylylene diisocyanate (TMXDI), or mixtures thereof.

In some embodiments, the bioresorbable aliphatic polyester copolymer is further prepared by copolymerizing the first and second polyester in the presence of the coupling agent and a catalyst, comprising organometallic catalyst, amine catalyst, or combinations thereof. The organometallic catalyst comprises dibutyltin dilaurate, tertbutyl titanate, dibutyltin, stannous octoate, or combinations thereof. The amine catalyst comprises N,N-Dimethylcyclohexylamine, 1,1,3,3-tertamethylguanidine, tetramethylethylenediamine, triethylene diamine, tripropylene glycol, N,N'-dimethylpiperazine, N,N,N',N'-tetramethyl-1,3-butanediamine, trimethylpiperazine, 1,4-bis(2-hydroxylpropyl)-2-methylpiperazine, N-hydroxyethylpiperazine, 1,3,5-tris(dimethylaminopropyl) hexahydrotriazine, dimethylbenzylamine, 4-ethylmorpholine, 2,2-dimorpholinoethyl ether, triethylamine, 2,2'-bis(2-ethyl-2-azobicycloether), diazobicyclooctane, dimethylaminopropylamine, diethylaminoethylamine, or combinations thereof.

Methods of preparing the bioresorbable aliphatic polyester copolymer are unlimited, and can be copolymerized by bulk polymerization, solution polymerization, emulsion polymerization, dispersion polymerization, suspension polymerization, or reactive extrusion.

For solution polymerization, the first and second polyesters, having the same repeat units but different molecular weights, are dissolved in an organic solvent. The coupling agent (and a catalyst) is added into the mixture to undergo a copolymerization with a reaction temperature of 30° C.~200° C., preferably 40° C.~150° C. The organic solvent is unlimited and can be N,N-dimethylformamide (DMF), N,N-dimethylacetamide (DMAc), dimethyl sulfoxide (DMSO), tetrahedrofuran (THF), chloroform, dichloromethane (DCM), 1,4-dioxane, benzene solvent, or combinations thereof. Regarding bulk polymerization, the first polyesters, second polyesters, and the coupling agent are mixed at a reaction temperature above their melt points, thereby performing a copolymerization directly. The reaction temperature of the process can be 40° C.~250° C., preferably 50° C.~200° C. Regarding bulk polymerization, the first polyesters, second polyesters, and the coupling agent are mixed at a reaction temperature above their melt points, thereby performing a copolymerization directly. The reaction temperature of the above process can be 40° C.~250° C., preferably 50° C.~200° C. Regarding reactive extrusion, a mixture of the first polyesters, second polyesters, and the coupling agent is directly fed into a twin-screw (or single-screw) extruder at 50° C.~250° C., preferably 60° C.~220° C. C.

The invention also provides an implantable medical device comprising the bioresorbable aliphatic polyester copolymer. The implantable device can serve as a medical device utilized in nerve repair, dura mater repair, ligament repair, tendon repair, hernia repair, rotator cuff repair, meniscal repair, muscle repair, joint repair, spinal repair, craniofacial repair, or maxiofacial repair. Specifically, the implantable medical device has a shape of a tube, multi-channel tube, film, filmic curl, pin, plank, or sponge.

Conventional nerve repair procedures restore continuity between proximal and distal nerve stumps. When a nerve gap is to be bridged, it may be necessary to utilize an intervening material. The most commonly used material is an autograft of a peripheral nerve harvested from the patient, e.g., a sural nerve autograft. The surgical repair procedure, however, is tedious and time-consuming. Further, the sural nerve harvested from a patient is not able to reach the target nerve site below the injury level, and the patient would sacrifice sense perception since a part of the sural nerve is taken out. Synthetic materials have been used to make tubes or conduits for guiding peripheral nerve regeneration, although results are not yet satisfactory for repairing nerve defects. An optimum nerve repair operation should have a porous structure and be bioresorbable material with superior mechanical properties and modifiable decomposition period.

The implantable device for nerve repair according to the invention is prepared by dissolving an aliphatic polyester copolymer of the invention in an organic solvent to obtain a bioresorbable polymer solution.

The organic solvent can be N,N-dimethylformamide (DMF), N,N-dimethylacetamide (DMAc), THF, chloroform, 1,4-dioxane, or combinations thereof.

Next, the bioresorbable polymer solution is applied to a surface of a cylindraceous mold and then reacted with a coagulator. After removal of the cylindraceous mol, a hollow and porous aliphatic polyester copolymer tube, serving as implantable device for nerve repair, is obtained. The thickness of the tube wall is 0.05 to 1.5 mm. The coagulator can be water or a mixture comprising water and an organic solvent, and the weight ratio between water and the organic solvent is 1:3~20:1. The organic solvent suitable for the invention can be amide, ketone, alcohol, or combinations thereof, preferably ketone or alcohol, such as N,N-dimethylformamide (DMF), N,N-dimethylacetamide (DMAc), acetone, methyl ethyl ketone (MEK), methanol, ethanol, propanol, isopropanol, or butanol.

In an embodiment of the invention, an oligomer with low molecular weight can be added into the bioresorbable polymer solution to serve as a pore former. Suitable oligomers can be polycaprolactone triol (PCLTL), polycaprolactone diol (PCLDL), polycaprolactone (PCL), polylactic acid (PLA), polyethylene glycol (PEG), polypropylene glycol (PPG), polytetramethylene glycol (PTMG), or combinations thereof.

The porosity (pore ratio) and pore size of the implantable device for nerve repair can be modified by adjusting the varieties and molecular weight of the oligomer, or weight ratio between the oligomer and aliphatic polyester copolymer. The oligomer can have a molecular weight between 200~4000. The weight ratio between the oligomer and aliphatic polyester copolymer can be 1:20~1:1, preferably 1:10~2:3. Particularly, the pores of the hollow aliphatic polyester copolymer tube serving as nerve repair device can be interconnected each other.

The nerve repair device guides the nerve axons in a predetermined direction and prevents entangling thereof. Since the nerve repair device is made of the aliphatic polyester copolymer of the invention, the nerve repair device can have a adjustable biodegradation period 3~12 months, avoiding nerve compression and foreign-body reaction.

The interconnected pores of the nerve repair device can provide a better microenvironment for cell aggregation along with nutrition and metabolite transfer.

Dura mater is a functionally significant structure in the anatomy of the central nervous system, forming a membrane system which envelops the entire central nervous system and protects it from external influences. The dura mater may require repair due to a number of causes, including trauma, inflammatory or neoplastic processes, surgical procedures, or congenital abnormalities. The need to close dural defects, especially following surgical procedures and in the presence of posttraumatic fistulae, has prompted a quest for the ideal dura mater substitute. These defects may result in postoperative complications, in particular, seepage of cerebrospinal fluid, infections, and resultant cerebral seizures, necessitating some form of dural graft procedure. As the primary closure of the dural defect often fails, the availability of a dural substitute to avoid the above complications is of great practical significance.

The invention provides an aliphatic polyester copolymer dural substitute and method for fabricating the same.

The aliphatic polyester copolymer dural substitute according to the invention can be prepared by the following steps. First, an aliphatic polyester copolymer of the invention and an oligomer are dissolved in an organic solvent to obtain a bioresorbable polymer solution. Next, the bioresorbable polymer solution is poured into a mold with a specific shape having rough or uneven surfaces and then reacted with a coagulator, wherein the peak-to valley height of the rough or uneven surfaces is between 10 μm amd 1000 μm, preferably between 20 μm and 500 μm. After separation from the mold, a porous and multi-layer aliphatic polyester copolymer dural substitute is obtained. The shape of the dural substitute can be a film with a thickness of 0.01~5 mm, preferable 0.1~3 mm.

The oligomer can be polycaprolactone triol (PCLTL), polycaprolactone diol (PCLDL), polycaprolactone (PCL), polylactic acid (PLA), polyethylene glycol (PEG), polypropylene glycol (PPG), polytetramethylene glycol (PTMG), or combinations thereof. The organic solvent can be N,N-dimethylformamide (DMF), N,N-dimethylacetamide (DMAc), THF, chloroform, 1,4-dioxane, or combinations thereof.

The porosity (pore ratio) and pore size of the dural substitute can be modified by adjusting the varieties and molecular weight of the oligomer, or weight ratio between the oligomer and aliphatic polyester copolymer. The oligomer can have a molecular weight between 200 and 4000. The weight ratio between the oligomer and aliphatic polyester copolymer can be 1:20~1:1, preferably 1:10~2:3. Particularly, the dural substitute can also have a smooth surface (non-porous or less porous surface) via the selection of coagulator. The coagulator can be water or a mixture comprising water and an organic solvent, and the weight ratio between water and the organic solvent is 1:3~20:1. The organic solvent suitable for the invention can be amide, ketone, alcohol, or combinations thereof, preferably ketone or alcohol, such as N,N-dimethylformamide (DMF), N,N-dimethylacetamide (DMAc), acetone, methyl ethyl ketone (MEK), methanol, ethanol, propanol, isopropanol, or butanol.

The dural substitute of the invention, comprising bioresorbable aliphatic polyester copolymer as disclosed, provides multi-layer and porous structures and properties of sufficient flexibility and elasticity. Specifically, the dural substitute of the invention has a multi-layer structure having a smooth surface preventing brain nerves from tissue adhesion with the dura mater substitute and having a rough surface facilitating the proliferation of dural tissue (such as Fibroblasts). Therefore, the dural substitute exhibits high bioresorbability, criteria of flexibility, inhibition of the cerebrospinal fluid leakage, and high mechanical strength.

Moreover, due to bioresorbability, the aliphatic polyester polymers of the invention are suitable for the fabrication of trash bag and other goods, substituting for non-biodegradable plastic.

The following examples are intended to demonstrate the invention more fully without limiting its scope, since numerous modifications and variations will be apparent to those skilled in the art.

Example 1

75 g of polycaprolactone having a molecular weight of 2000 ($PCL_{2000}$) was put into a bottle and dissolved in 58.5 g of dimethylacetamide (DMAc). Then, 22.18 g $H_{12}MDI$ as a coupling agent and 60 mg dibutyltin dilaurate (DBTDL) as a catalyst were added into the bottle. After stirring at 60° C., 25 g of polycaprolactone having a molecular weight of 530 ($PCL_{530}$) dissolved in 58.5 g of DMAc was added dropwise into the bottle with a flow rate of 2 ml/min. The adhesion of the mixture in the bottle were measured, and $H_{12}MDI$, DMAc, and DBTDL were optionally added into the bottle. After reacting for 8 hours, the total additive amounts of $H_{12}MDI$, DBTDL, and DMAc were respectively 31.93 g, 0.4 g, and 234 g. Finally, 0.3 g of di-n-butylamine (DBA) was added into the bottle to consume the remained isocyanate, thereby terminating the copolymerization. The reaction according to Example 1 is shown below.

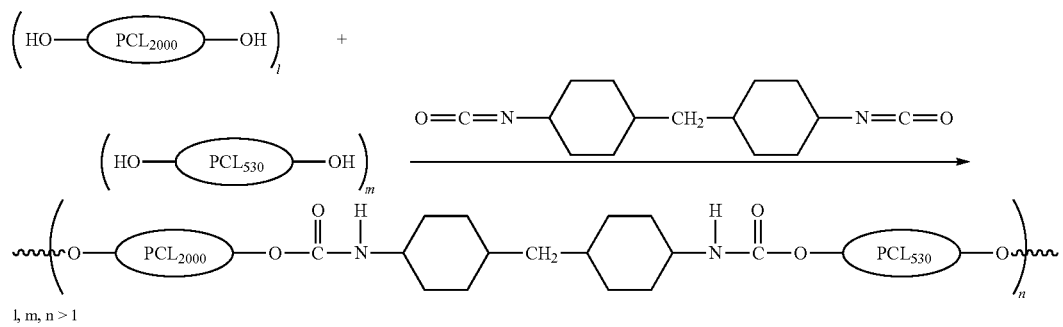

Next, the obtained copolymer with a solid content of 20% was coated on a glass substrate and baked at 80° C. for 3 hours to remove DMAc. The coating was scraped off the substrate, and the obtained powder was extracted with ethyl ether by soxhlet extractor for 24 hours. The $^1H$-NMR spectrum, $^{13}C$-NMR spectrum, and FT-IR spectrum of the obtained product are respectively shown in FIGS. 1, 2, and 3. In FIG. 1, the peaks c, d, e, g, h, i, and j show the hydrogen singles of —$CH_2$— of caprolactone, and the peaks a and b show the hydrogen singles of —NH— of urethane group, as shown below:

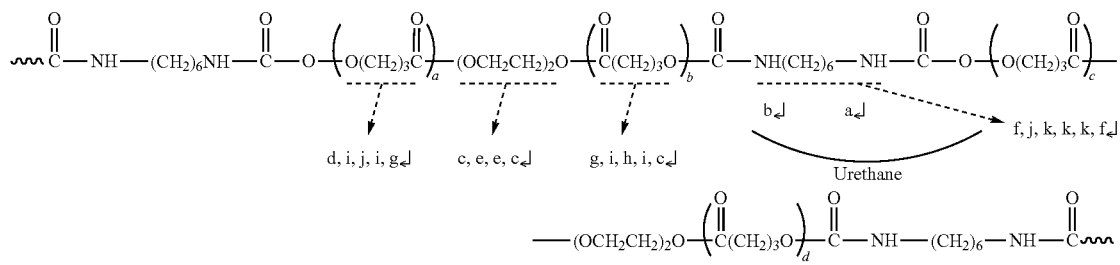

a, b, c, and d≧1

Figure 2:
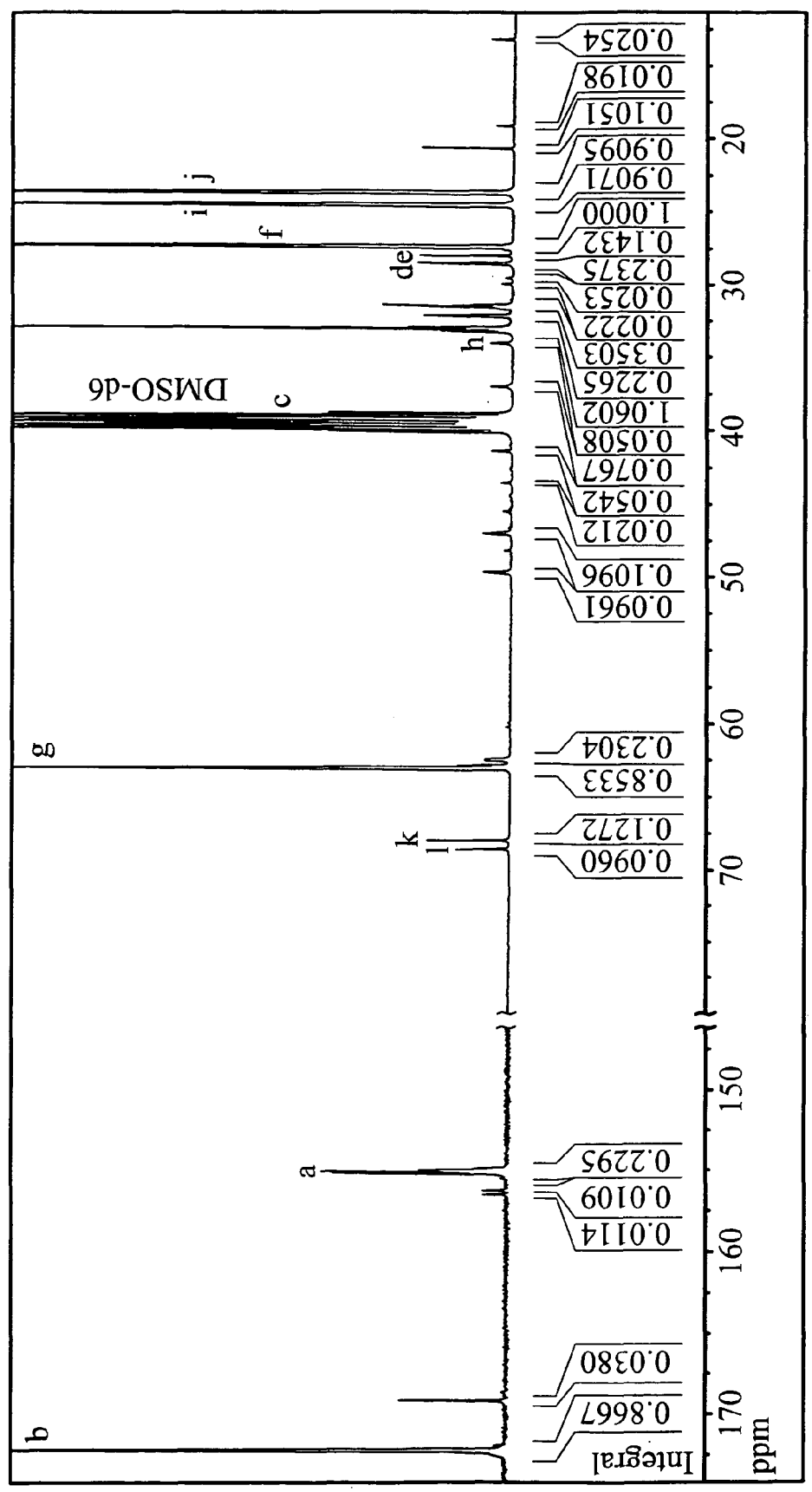
FIG. 2 shows the $^{13}$C-NMR spectrum of the aliphatic polyester copolymer of Example 1.

In FIG. 2, peaks c, d, e, and f show the carbon singles of $H_{12}$MDI (coupling agent), peaks a and b show the carbon singles of carbonyl group, peaks d, f, g, h, i, j, k, and l show the carbon singles of caprolactone, and peak DMSO shows the carbon single of solvent DMSO, show as below:

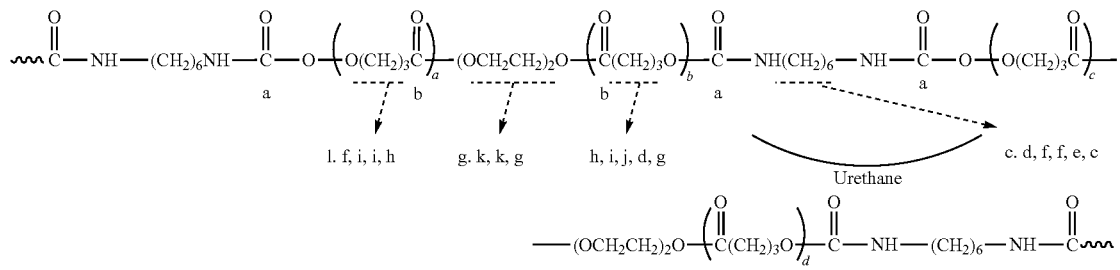

a, b, c, and d≧1

Figure 3:
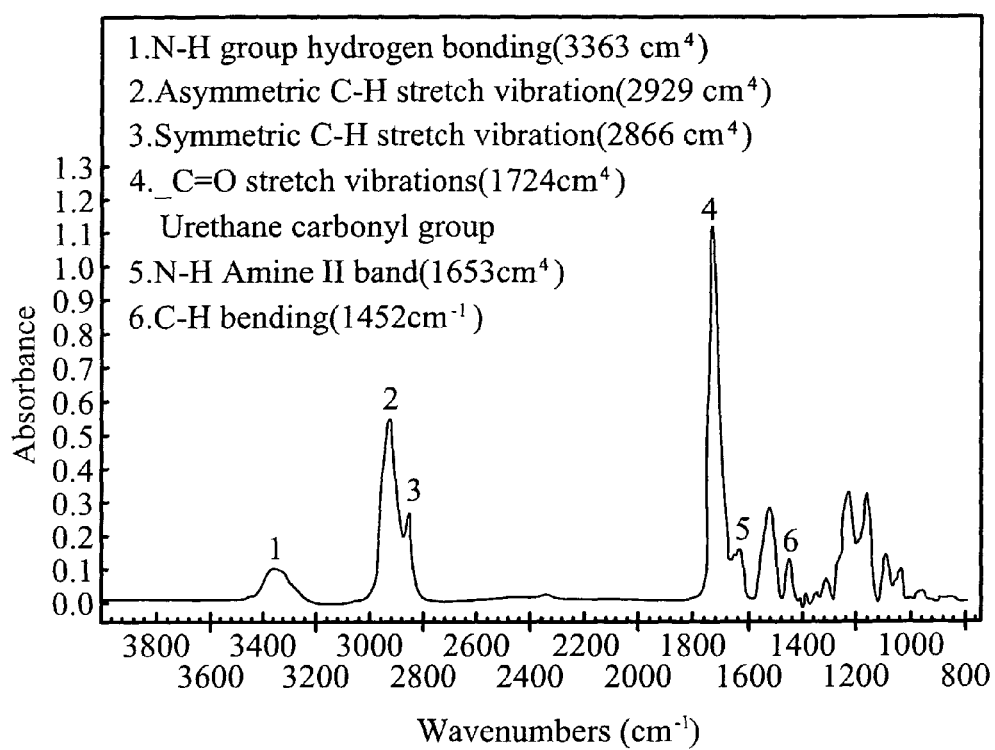
FIG. 3 shows the FT-IR spectrum of the aliphatic polyester copolymer of Example 1.

In FIG. 3, peaks 1, 2, 3, 4, 5 and 6, show the FT-IR peak assignment of aliphatic polyester copolymer. (Example 1)

Further, the weight average molecular weights (Mw), polydispersity index (PDI), glass transition temperature (Tg), melt temperature (Tm), and crystallinity of the obtained product were measured and are shown in Table 1.

TABLE 1

| Content | Mw | PDI | Tg | Tm | crystallinity |
|---|---|---|---|---|---|
| PCL$_{2000}$:PCL$_{530}$ = 75:25 (by weight) | 81,377 | 2.4 | −29.7° C. | | Amorphous |

The crystallinity was characterized using the following formula:

C=ΔH/(wPCL×ΔHref),

C: crystallinity,
wPCL: the weight fraction of PCL in the copolymer,
ΔHref: 136.1 J/g, the reference melting enthalpy of 100% crystalline PCL.

Example 2

50 g of polycaprolactone having a molecular weight of 2000 (PCL$_{2000}$) was put into a bottle and dissolved in 58.5 g of dimethylacetamide (DMAc). Then, 31.28 g $H_{12}$MDI as a coupling dddddd agent and 60 mg dibutyltin dilaurate (DBTDL) as a catalyst were added into the bottle. After stirring at 60° C., 50 g of polycaprolactone having a molecular weight of 530 (PCL$_{530}$) dissolved in 58.5 g of DMAc was added dropwise into the bottle with a flow rate of 2 ml/min. The adhesion of the mixture in the bottle were measured, and $H_{12}$MDI, DMAc, and DBTDL were optionally added into the bottle. After reacting for 8 hours, the total additive amounts of $H_{12}$MDI, DBTDL, and DMAc were respectively 38.16 g, 0.4 g, and 234 g. Finally, 0.1 g of di-n-butylamine (DBA) was added into the bottle to consume the remained isocyanate, thereby terminating the copolymerization.

Next, the obtained copolymer with a solid content of 20% was coated on a glass substrate and baked at 80° C. for 3 hours to remove DMAc. The coating was scraped off the substrate, and the obtained powder was extracted with ethyl ether by soxhlet extractor for 24 hours. The weight average molecular weights (Mw), polydispersity index (PDI), glass transition temperature (Tg), melt temperature (Tm), and crystallinity of the obtained product were measured and are shown in Table 2.

TABLE 2

| Content | Mw | PDI | Tg | Tm | crystallinity |
|---|---|---|---|---|---|
| PCL$_{2000}$:PCL$_{530}$ = 50:50 (by weight) | 96,598 | 2.5 | −39.5° C. | | Amorphous |

Example 3

25 g of polycaprolactone having a molecular weight of 2000 (PCL2000) was put into a bottle and dissolved in 58.5 g of dimethylacetamide (DMAc). Then, 40.35 g H12MDI as a coupling agent and 60 mg dibutyltin dilaurate (DBTDL) as a catalyst were added into the bottle. After stirring at 60° C., 75 g of polycaprolactone having a molecular weight of 530 (PCL530) dissolved in 58.5 g of DMAc was added dropwise into the bottle with a flow rate of 2 ml/min. The adhesion of the mixture in the bottle were measured, and H12MDI, DMAc, and DBTDL were optionally added into the bottle. After reacting for 8 hours, the total additive amounts of H12MDI, DBTDL, and DMAc were respectively 45.19 g, 0.4 g, and 234 g. Finally, 0.2 g of di-n-butylamine (DBA) was added into the bottle to consume the remained isocyanate, thereby terminating the copolymerization.

Next, the obtained copolymer with a solid content of 20% was coated on a glass substrate and baked at 80° C. for 3 hours to remove DMAc. The coating was scraped off the substrate, and the obtained powder was extracted with ethyl ether by soxhlet extractor for 24 hours. The weight average molecular weights (Mw), polydispersity index (PDI), glass transition temperature (Tg), melt temperature (Tm), and crystallinity of the obtained product were measured and are shown in Table 3.

TABLE 3

| Content | Mw | PDI | Tg | Tm | crystallinity |
|---|---|---|---|---|---|
| $PCL_{2000}$:$PCL_{530}$ = 25:75 (by weight) | 85,157 | 2.1 | −27.3° C. | | Amorphous |

Example 4

75 g of polycaprolactone having a molecular weight of 10000 ($PCL_{10000}$) was put into a bottle and dissolved in 58.5 g of dimethylacetamide (DMAc). Then, 14.32 g $H_{12}MDI$ as a coupling agent and 60 mg dibutyltin dilaurate (DBTDL) as a catalyst were added into the bottle. After stirring at 60° C., 25 g of polycaprolactone having a molecular weight of 530 ($PCL_{530}$) dissolved in 58.5 g of DMAc was added dropwise into the bottle with a flow rate of 2 ml/min. The adhesion of the mixture in the bottle were measured, and $H_{12}MDI$, DMAc, and DBTDL were optionally added into the bottle. After reacting for 8 hours, the total additive amounts of $H_{12}MDI$, DBTDL, and DMAc were respectively 18.62 g, 0.4 g, and 234 g. Finally, 0.2 g of di-n-butylamine (DBA) was added into the bottle to consume the remaining isocyanate, thereby terminating the copolymerization.

Next, the obtained copolymer with a solid content of 20% was coated on a glass substrate and baked at 80° C. for 3 hours to remove DMAc. The coating was scraped off the substrate, and the obtained powder was extracted with ethyl ether by soxhlet extractor for 24 hours. The weight average molecular weights (Mw), polydispersity index (PDI), glass transition temperature (Tg), melt temperature (Tm), and crystallinity of the obtained product were measured and are shown in Table 4.

TABLE 4

| Content | Mw | PDI | Tg | Tm | crystallinity |
|---|---|---|---|---|---|
| $PCL_{10000}$:$PCL_{530}$ = 75:25 (by weight) | 111,523 | 2.6 | −60.3° C. | 60.2° C. | 44.8% |

Example 5

100 g of polycaprolactone having a molecular weight of 10000 ($PCL_{10000}$) was put into a bottle and dissolved in 117 g of dimethylacetamide (DMAc). Then, 62.62 g $H_{12}MDI$ as a coupling agent and 60 mg dibutyltin dilaurate (DBTDL) as a catalyst were added into the bottle. After stirring at 60° C., 100 g of polycaprolactone having a molecular weight of 530 ($PCL_{530}$) dissolved in 117 g of DMAc was added dropwise into the bottle with a flow rate of 2 ml/min. The adhesion of the mixture in the bottle were measured, and $H_{12}MDI$, DMAc, and DBTDL were optionally added into the bottle. After reacting for 8 hours, the total additive amounts of $H_{12}MDI$, DBTDL, and DMAc were respectively 67.62 g, 0.8 g, and 468 g. Finally, 0.2 g of di-n-butylamine (DBA) was added into the bottle to consume the remained isocyanate, thereby terminating the copolymerization.

Next, the obtained copolymer with a solid content of 20% was coated on a glass substrate and baked at 80° C. for 3 hours to remove DMAc. The coating was scraped off the substrate, and the obtained powder was extracted with ethyl ether by soxhlet extractor for 24 hours. The weight average molecular weights (Mw), polydispersity index (PDI), glass transition temperature (Tg), melt temperature (Tm), and crystallinity of the obtained product were measured and are shown in Table 5.

TABLE 5

| Content | Mw | PDI | Tg | Tm | crystallinity |
|---|---|---|---|---|---|
| $PCL_{10000}$:$PCL_{530}$ = 50:50 (by weight) | 84,320 | 2.4 | −55.9° C. | 37.8° C. | 17.7% |

Example 6

25 g of polycaprolactone having a molecular weight of 10000 ($PCL_{10000}$) was put into a bottle and dissolved in 58.5 g of dimethylacetamide (DMAc). Then, 37.73 g $H_{12}MDI$ as a coupling agent and 60 mg dibutyltin dilaurate (DBTDL) as a catalyst were added into the bottle. After stirring at 60° C., 75 g of polycaprolactone having a molecular weight of 530 ($PCL_{530}$) dissolved in 58.5 g of DMAc was added dropwise into the bottle with a flow rate of 2 ml/min. The adhesion of the mixture in the bottle were measured, and $H_{12}MDI$, DMAc, and DBTDL were optionally added into the bottle. After reacting for 8 hours, the total additive amounts of $H_{12}MDI$, DBTDL, and DMAc were respectively 49.8 g, 0.4 g, and 234 g. Finally, 0.3 g of di-n-butylamine (DBA) was added into the bottle to consume the remaining isocyanate, thereby terminating the copolymerization.

Next, the obtained copolymer with a solid content of 20% was coated on a glass substrate and baked at 80° C. for 3 hours to remove DMAc. The coating was scraped off the substrate, and the obtained powder was extracted with ethyl ether by soxhlet extractor for 24 hours. The weight average molecular weights (Mw), polydispersity index (PDI), glass transition temperature (Tg), melt temperature (Tm), and crystallinity of the obtained product were measured and are shown in Table 6.

TABLE 6

| Content | Mw | PDI | Tg | Tm | crystallinity |
|---|---|---|---|---|---|
| $PCL_{10000}$:$PCL_{530}$ = 25:75 (by weight) | 88,764 | 2.4 | −19.0° C. | | Amorphous |

Example 7

80 g of polycaprolactone having a molecular weight of 10000 ($PCL_{10000}$) was put into a bottle and dissolved in 58.5 g of dimethylacetamide (DMAc). Then, 4.72 g $H_{12}MDI$ as a coupling agent and 60 mg dibutyltin dilaurate (DBTDL) as a catalyst were added into the bottle. After stirring at 60° C., 20 g of polycaprolactone having a molecular weight of 2000 ($PCL_{2000}$) dissolved in 58.5 g of DMAc was added dropwise into the bottle with a flow rate of 2 ml/min. The adhesion of the mixture in the bottle were measured, and $H_{12}MDI$, DMAc, and DBTDL were optionally added into the bottle. After reacting for 8 hours, the total additive amounts of $H_{12}MDI$, DBTDL, and DMAc were respectively 7.31 g, 0.4 g, and 234 g. Finally, 0.2 g of di-n-butylamine (DBA) was added into the bottle to consume the remaining isocyanate, thereby terminating the copolymerization.

Next, the obtained copolymer with a solid content of 20% was coated on a glass substrate and baked at 80° C. for 3 hours to remove DMAc. The coating was scraped off the substrate, and the obtained powder was extracted with ethyl ether by soxhlet extractor for 24 hours. The weight average molecular weights (Mw), polydispersity index (PDI), glass transition temperature (Tg), melt temperature (Tm), and crystallinity of the obtained product were measured and are shown in Table 7.

TABLE 7

| Content | Mw | PDI | Tg | Tm | crystallinity |
|---|---|---|---|---|---|
| $PCL_{10000}:PCL_{2000}$ = 80:20 (by weight) | 984,567 | 1.65 | −49.9° C. | 58.6° C. | 31.3% |

Example 8

25 g of polycaprolactone having a molecular weight of 2000 ($PCL_{2000}$) was put into a bottle and dissolved in 58.5 g of dimethylacetamide (DMAc). Then, 40.35 g $H_{12}MDI$ as a coupling agent and 1 g triethylene diamine (TEDA) as a catalyst were added into the bottle. After stirring at 85° C., 75 g of polycaprolactone having a molecular weight of 530 ($PCL_{530}$) dissolved in 58.5 g of DMAc was added dropwise into the bottle with a flow rate of 2 ml/min. The adhesion of the mixture in the bottle were measured, and $H_{12}MDI$, DMAc, and TEDA were optionally added into the bottle. After reacting for 48 hours, the total additive amounts of $H_{12}MDI$, TEDA, and DMAc were respectively 45.19 g, 6 g, and 234 g. Finally, 0.3 g of di-n-butylamine (DBA) was added into the bottle to consume the remaining isocyanate, thereby terminating the copolymerization.

Next, the obtained copolymer with a solid content of 20% was coated on a glass substrate and baked at 80° C. for 3 hours to remove DMAc. The coating was scraped off the substrate, and the obtained powder was extracted with ethyl ether by soxhlet extractor for 24 hours. The weight average molecular weights (Mw), polydispersity index (PDI), glass transition temperature (Tg), melt temperature (Tm), and crystallinity of the obtained product were measured and are shown in Table 8.

TABLE 8

| Content | Mw | PDI |
|---|---|---|
| $PCL_{2000}:PCL_{530}$ = 25:75 (by weight) | 103,471 | 2.1 |

Example 9

25 g of polycaprolactone having a molecular weight of 10000 ($PCL_{10000}$) was put into a bottle and dissolved in 58.5 g of dimethylacetamide (DMAc). Then, 37.73 g $H_{12}MDI$ as a coupling agent and 1 g triethylene diamine (TEDA) as a catalyst were added into the bottle. After stirring at 80° C., 75 g of polycaprolactone having a molecular weight of 530 ($PCL_{530}$) dissolved in 58.5 g of DMAc was added dropwise into the bottle with a flow rate of 2 ml/min. The adhesion of the mixture in the bottle was measured, and $H_{12}MDI$, DMAc, and TEDA were optionally added into the bottle. After reacting for 48 hours, the total additive amounts of $H_{12}MDI$, TEDA, and DMAc were respectively 49.8 g, 6 g, and 234 g. Finally, 0.1 g of di-n-butylamine (DBA) was added into the bottle to consume the remaining isocyanate, thereby terminating the copolymerization.

Next, the obtained copolymer with a solid content of 20% was coated on a glass substrate and baked at 80° C. for 3 hours to remove DMAc. The coating was scraped off the substrate, and the obtained powder was extracted with ethyl ether by soxhlet extractor for 24 hours. The weight average molecular weights (Mw), polydispersity index (PDI), glass transition temperature (Tg), melt temperature (Tm), and crystallinity of the obtained product were measured and are shown in Table 9.

TABLE 9

| Content | Mw | PDI |
|---|---|---|
| $PCL_{10000}:PCL_{530}$ = 25:75 (by weight) | 195,500 | 1.9 |

Example 10

75 g of polycaprolactone having a molecular weight of 2000 ($PCL_{2000}$) and 25 g of polycaprolactone having a molecular weight of 530 ($PCL_{530}$) were put into a reactive tank and stirred at 100° C. Next, 31.93 g of $H_{12}MDI$ and 0.1 g of dibutyltin dilaurate (DBTDL) was added into the mixture. After stirring at a speed of 30 rpm for 15 min, the result was poured into a mold and put in an oven at 90° C. for 8 hours. The obtained product was smashed, and the weight average molecular weights (Mw) and polydispersity index (PDI) thereof was measured, as shown in Table 10.

TABLE 10

| Content | Mw | PDI |
|---|---|---|
| $PCL_{2000}:PCL_{530}$ = 75:25 (by weight) | 184,233 | 1.85 |

Example 11

50 g of polycaprolactone having a molecular weight of 2000 ($PCL_{2000}$) and 50 g of polycaprolactone having a molecular weight of 530 ($PCL_{530}$) were put into a reactive tank and stirred at 100° C. Next, 38.16 g of $H_{12}MDI$ and 0.1 g of dibutyltin dilaurate (DBTDL) was added into the mixture. After stirring at a speed of 300 rpm for 5 min, the result was poured into a mold and put in an oven at 80° C. for 6 hours. The obtained product was crushed, and the weight average molecular weights (Mw) and polydispersity index (PDI) thereof were measured, as shown in Table 11.

TABLE 11

| Content | Mw | PDI |
|---|---|---|
| $PCL_{2000}:PCL_{530}$ = 50:50 (by weight) | 191,735 | 1.81 |

Example 12

25 g of polycaprolactone having a molecular weight of 2000 ($PCL_{2000}$) and 75 g of polycaprolactone having a molecular weight of 530 ($PCL_{530}$) were put into a reactive tank and stirred at 100° C. Next, 43.58 g of $H_{12}MDI$ and 0.1 g of dibutyltin dilaurate (DBTDL) was added into the mixture. After stirring at a speed of 30 rpm for 15 min, the result was poured into a mold and put in an oven at 90° C. for 8 hours. The obtained product was smashed, and the weight average molecular weights (Mw) and polydispersity index (PDI) thereof was measured, as shown in Table 12.

TABLE 12

| Content | Mw | PDI |
|---|---|---|
| $PCL_{2000}$:$PCL_{530}$ = 25:75 (by weight) | 36,715 | 2.12 |

Example 13

Preparation of Short-Chain L-Lactide Diol (A)

100 g of L-lactide was put into a bottle and completely melted at 110° C. Next, 2.87 g ethyl glycol (EG) and 1.5 g (0.5 mol %) stannous octanoate were put into the bottle, wherein the molar ratio between L-lactide and EG was 15:1. After heating at 140° C. for 6 hours in a nitrogen purged oven, the result was dissolved in dichloromethane and precipitated in diethyl ether. After drying, a L-lactide diol (A) was obtained, and the weight average molecular weight (Mw) and polydispersity index (PDI) thereof were measured, as shown in Table 13.

Preparation of Long-Chain L-Lactide Diol (B)

100 g of L-lactide was put into a bottle and completely melted at 110° C. Next, 2.15 g ethyl glycol (EG) and 1.48 g (0.5 mol %) stannous octanoate were put into the bottle, wherein the molar ratio between L-lactide and EG was 20:1. After heating at 140° C. for 6 hours in a nitrogen purged oven, the result was dissolved in dichloromethane and precipitated in diethyl ether. After drying, a L-lactide diol (B) was obtained, and the weight average molecular weights (Mw) and polydispersity index (PDI) thereof were measured, as shown in Table 13.

TABLE 13

| Content | Content | Mw | PDI |
|---|---|---|---|
| Short-chain L-lactide diol (A) | Lactide:EG = 15:1 (molar ratio) | 3,781 | 1.15 |
| Long-chain L-lactide diol (B) | Lactide:EG = 20:1 (molar ratio) | 4,569 | 1.17 |

Preparation of L-Lactide Based Aliphatic Polyester Copolymer 50 g of short-chain L-lactide diol (A) having a molecular weight of 3,781 ($PLA_{3781}$) and 50 g of long-chain L-lactide diol (B) having a molecular weight of 4,569 ($PLA_{4569}$) were put into a reactive tank and stirred at 190° C. Next, 6.63 g of $H_{12}MDI$ and 0.1 g of dibutyltin dilaurate (DBTDL) was added into the mixture. After stirring at a speed of 50 rpm for 5 min, the result was poured into a mold and put in an oven at 120° C. for 6 hours. The obtained product was crushed, and the weight average molecular weights (Mw) and polydispersity index (PDI) thereof were measured, as shown in Table 14.

TABLE 14

| Content | Mw | PDI |
|---|---|---|
| $PLA_{3781}$:$PLA_{4569}$ = 50:50 (by weight) | 26,585 | 2.35 |

Example 14

200 g of polycaprolactone having a molecular weight of 2000 ($PCL_{2000}$) and 200 g of polycaprolactone having a molecular weight of 10000 ($PCL_{10000}$) were put into a reactive tank and stirred at 100° C. Next, 47.16 g of $H_{12}MDI$ and 0.6 g of dibutyltin dilaurate (DBTDL) was added into the mixture. The result was fed into a co-rotating twin-screw extruder with L/D of 48 at a speed of 50 ml/min and screw configuration designed at 30 rpm, thereby performing a copolymerization. The screw was held at 150° C.~180° C. to melt the polycaprolactone, and the die held at 60° C. The obtained product was crushed, and the weight average molecular weights (Mw) and polydispersity index (PDI) thereof were measured, as shown in Table 15.

TABLE 15

| Content | Mw | PDI |
|---|---|---|
| $PCL_{2000}$:$PCL_{10000}$ = 50:50 (by weight) | 68,697 | 2.34 |

Example 15

Figure 4:
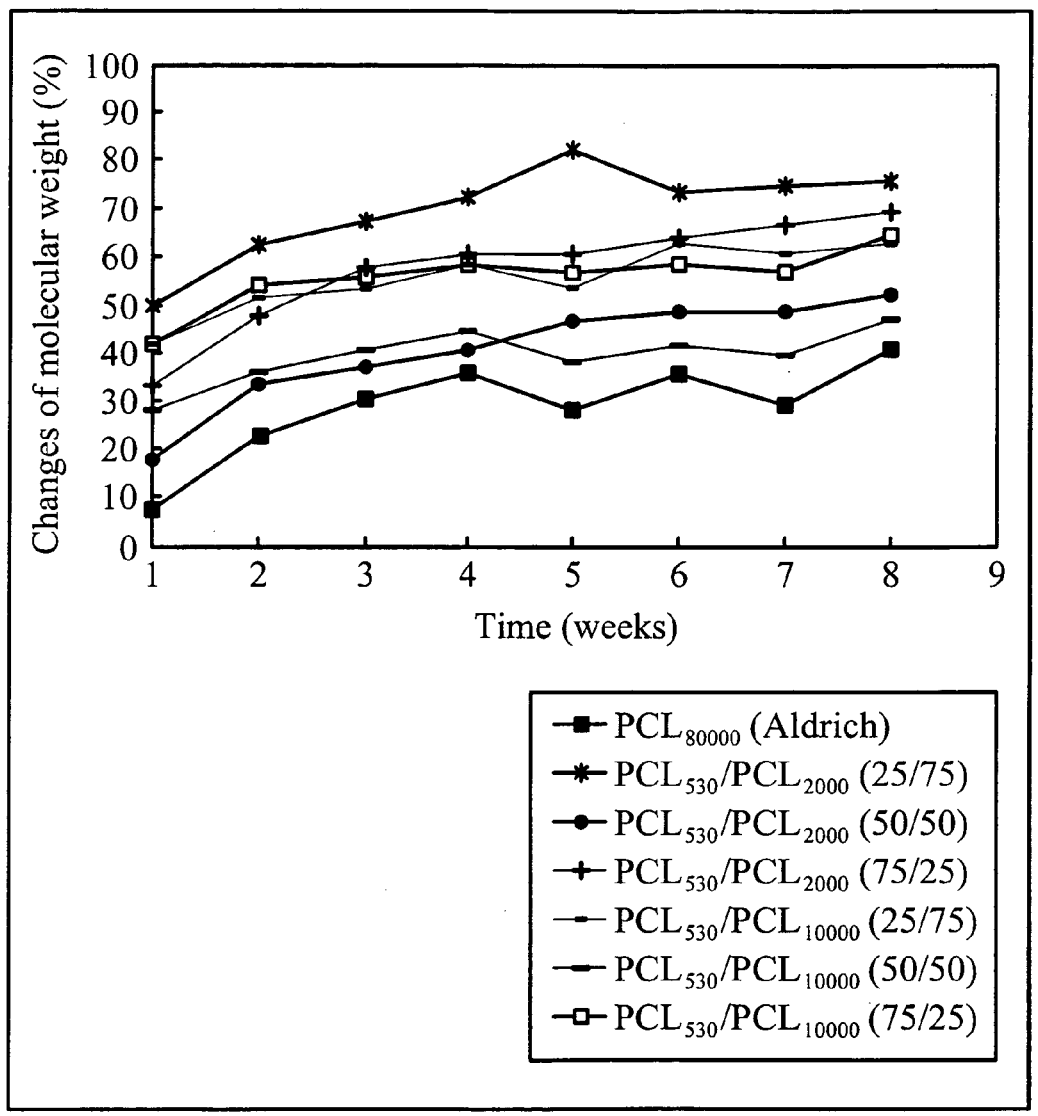
FIG. 4 is a graph plotting molecular weight changes against time of in-vitro degradation tests.

The in-vitro accelerated degradation of the aliphatic polyester copolymer of the invention was estimated by the method as below. The obtained copolymers of Examples 1~6 and a polycaprolactone having a molecular weight of 80000 (sold and manufactured by Aldrich Co., Ltd) were respectively employed to fabricate a 20×20 mm test piece with a thickness of 0.2 mm. Next, each test piece was put into an individual air-tight vial with 15 ml phosphate buffer saline (PBS). The vials were stirred with a speed of 20 rpm at 50±1° C. The relationship between molecular weight changes of each test piece and standing time is shown in FIG. 4. Accordingly, the biodegradation period of the aliphatic polyester copolymers of the invention depends on the difference of the weight average molecular weights and the weight ratio between the used polyesters, and is optionally adjustable.

Example 16

Figure 5A:
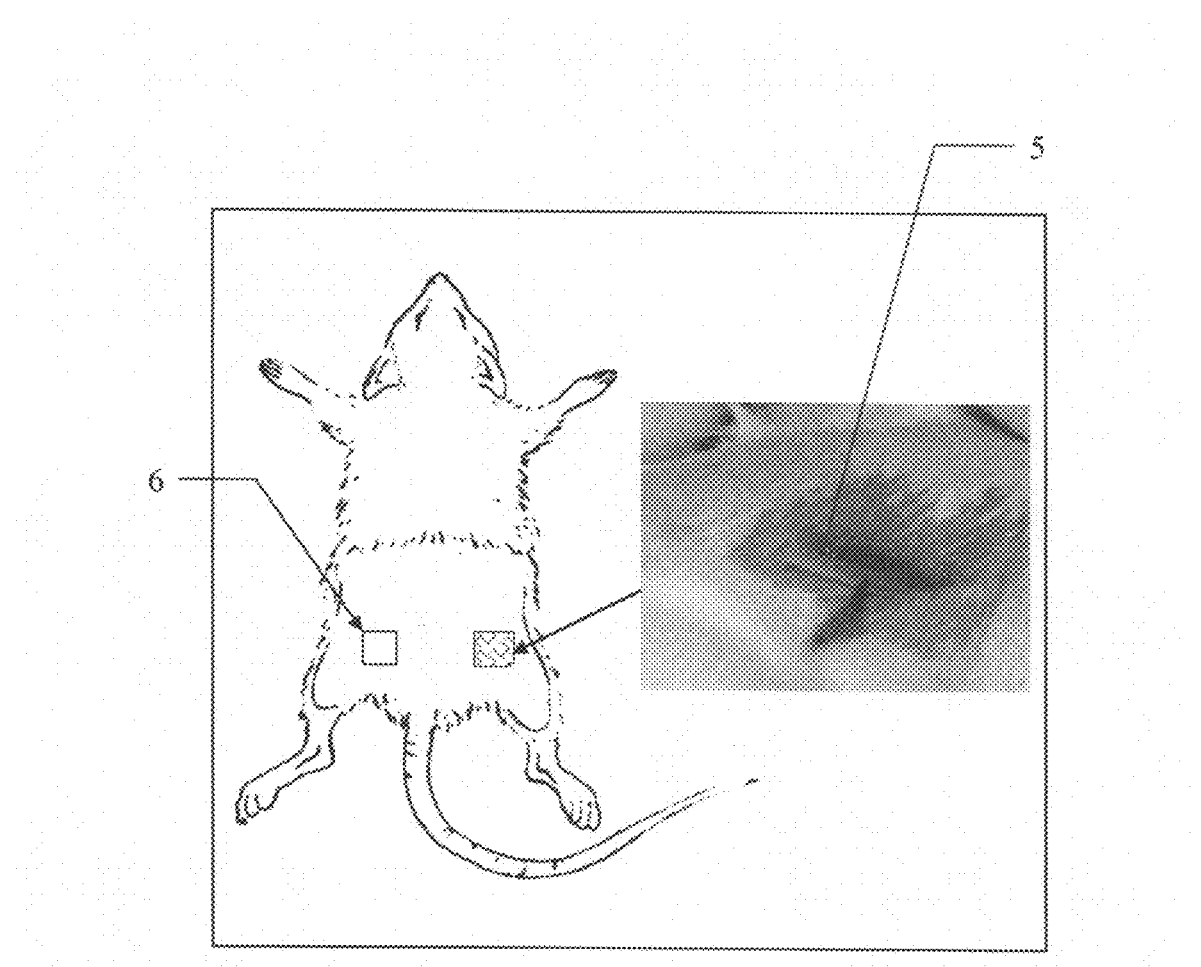
FIG. 5a is a schematic diagram showing an in-vivo degradation test as disclosed in Example 16.
Figure 5B:
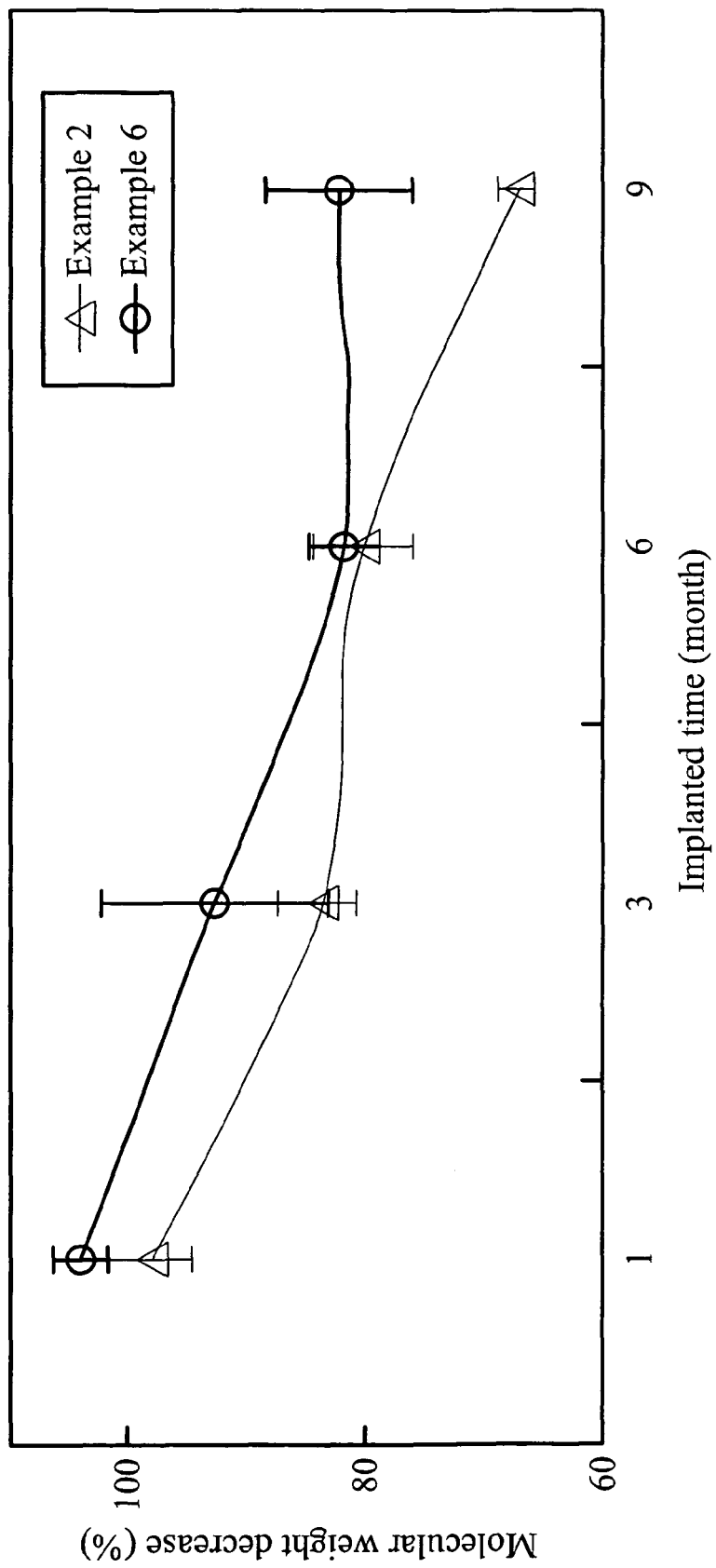
FIG. 5b is a graph plotting molecular weight changes against time of in-vivo degradation tests as disclosed in Example 16.

The in-vivo degradation of the aliphatic polyester copolymer of the invention was estimated by the method as below. As shown in FIG. 5a, adult Sprague Dawley rats 10 (200~250 g) were deeply anesthetized with chloral hydrate (400 mg/kg), and received a bilateral nerve crushing operation. The left side 6 of the rats serves as a control group. The obtained copolymers of Examples 2 and Examples 5 were respectively employed to fabricate a 12×5 mm test piece with a thickness of 0.5 mm, and the test pieces 5 were implanted into the rats. One month, three months, six months, and nine months after surgery, the test pieces 5 were take out of the rats and the molecular weight thereof was measured. The relationship between molecular weight changes of each test piece and standing time is shown in FIG. 5b.

Example 17

Figure 6:
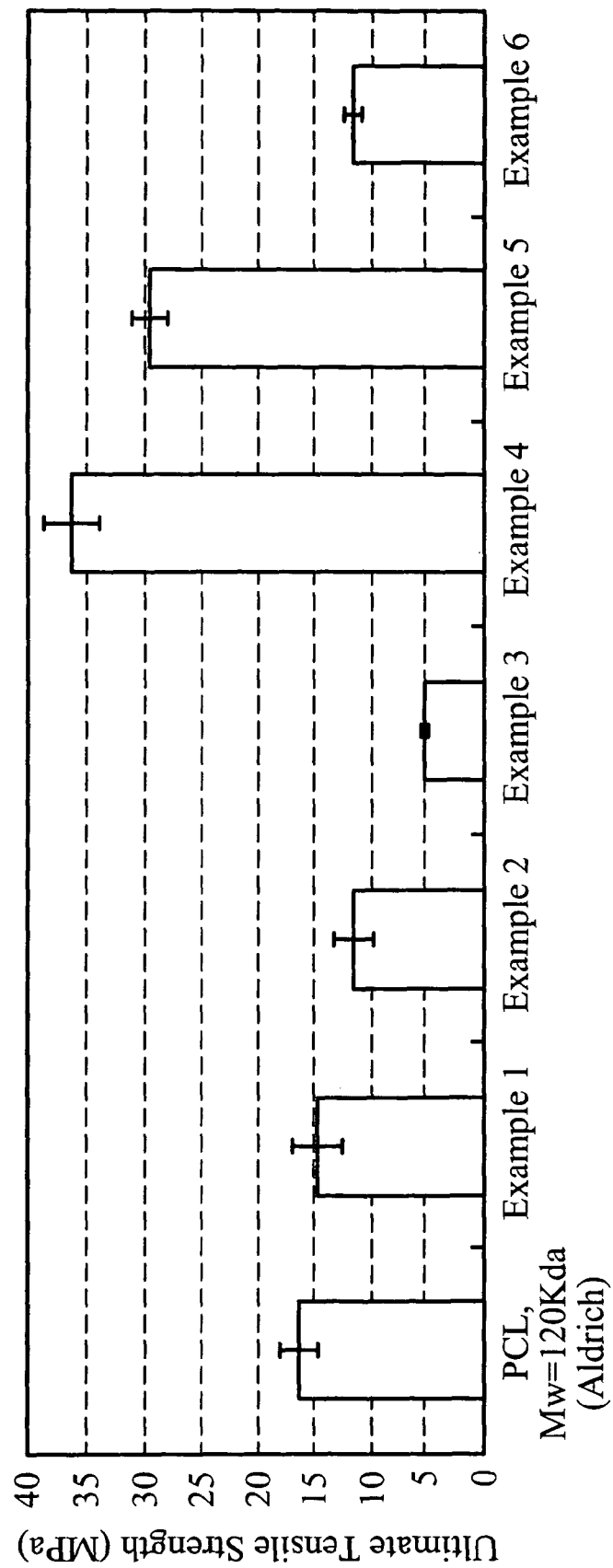
FIG. 6 is a graph plotting tensile strengths of the copolymer of Examples 1~6 and conventional polycaprolactone.
Figure 7:
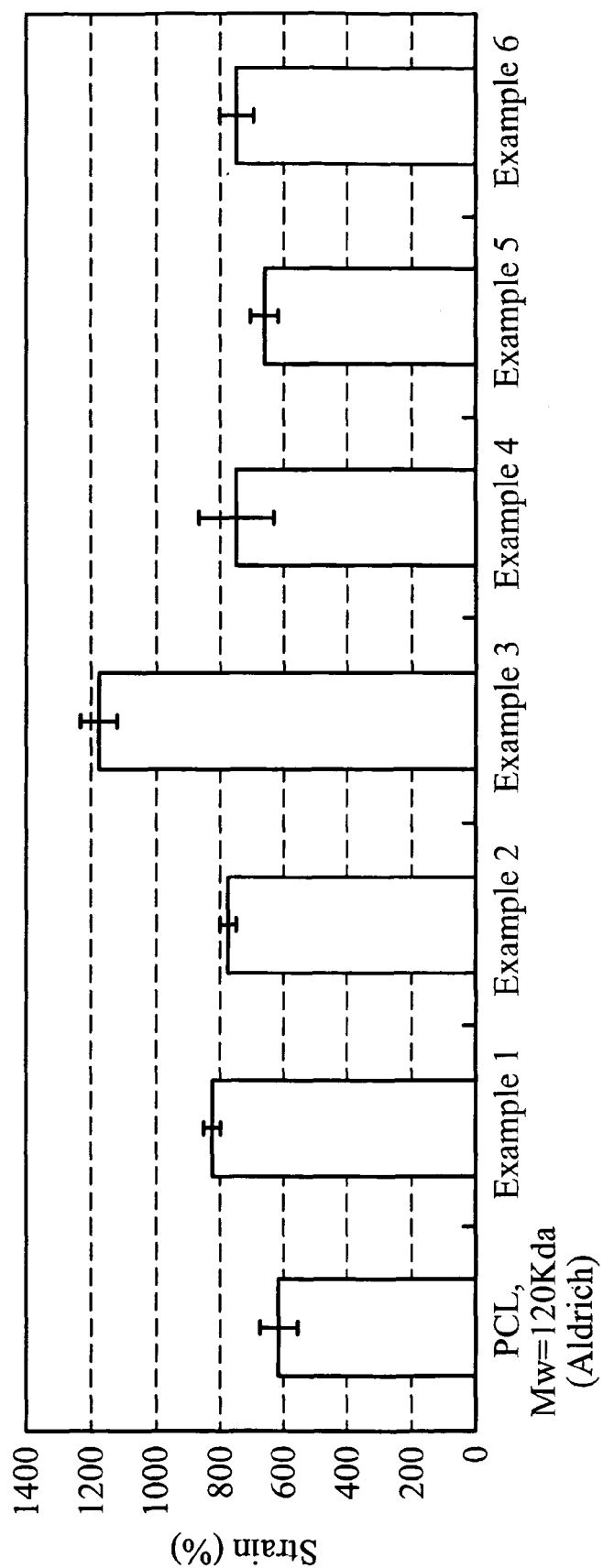
FIG. 7 is a graph plotting elongation of the copolymer of Examples 1~6 and conventional polycaprolactone.

The mechanical properties of the aliphatic polyester copolymer of the invention were estimated by the method as below. The obtained copolymers of Examples 1~6 and a polycaprolactone having a molecular weight of 120 Kda (sold and manufactured by Aldrich Co., Ltd) were respectively employed to fabricate a dumbbell-shaped test piece and measured through tensile and elongation strength tests conforming to ASTM D638 via an universal material testing machine (Instron 4467) equipped with a 500 N load cell, wherein the extending rate was 150 mm/min. The results are shown in FIGS. 6 and 7.

Preparation of Implantable Medical Device (Nerve Conduit) for Nerve Repair

Example 18

20 g of the obtained copolymer of Example 5 and 20 g of polyethylene glycol having a molecular weight of 300 (PEG300) were dissolved in 60 g of DMAc, forming an uniform polymer gel. Next, the gel was poured into a tubular coater with an internal diameter of 2.2 mm. Next, a rod with an external diameter of 1.5 mm inserted into the coater, resulting in a coating of the polymer gel, with a thickness of 0.35 mm, surrounding the rod.

Next, the rod with the gel coating was put into a coagulator, such as water, and the gel coating was solidified to form a porous hollow aliphatic polyester copolymer tube. After immersion in 40% ethanol for 2 hours, the porous hollow polyester tube was then washed with water for 2 hours, and dried. The porous hollow aliphatic polyester copolymer tube was then identified by scanning electron microscopy, it being observed that the pores of the hollow polyester tube were interconnected. Due to the bioresorbability, the porous hollow polyester tube can serve as an implantable medical device for nerve repair.

Figure 8A:
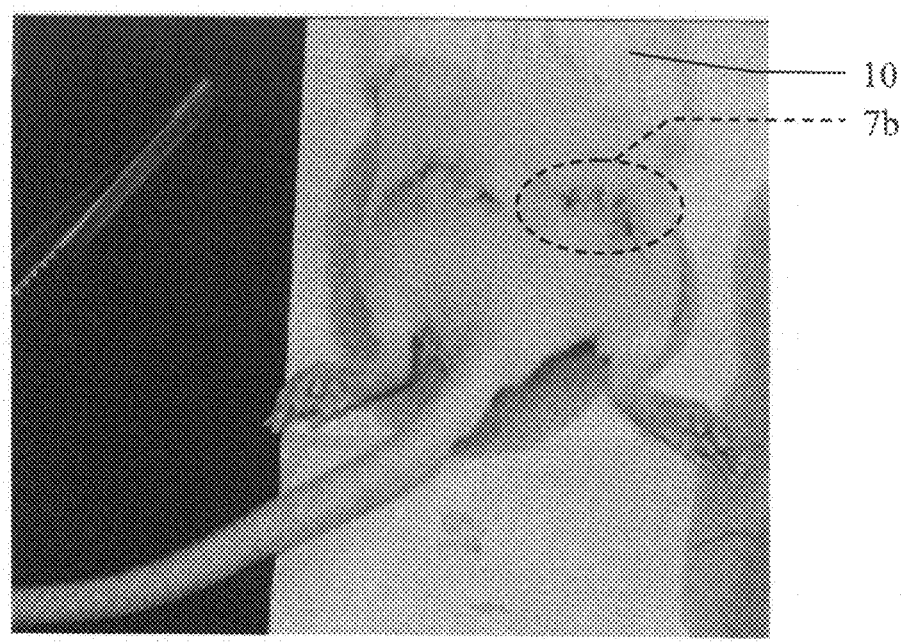
FIGS. 8a and 8b are schematic diagrams of rat sciatic nerve regeneration test of Example 18.
Figure 8B:
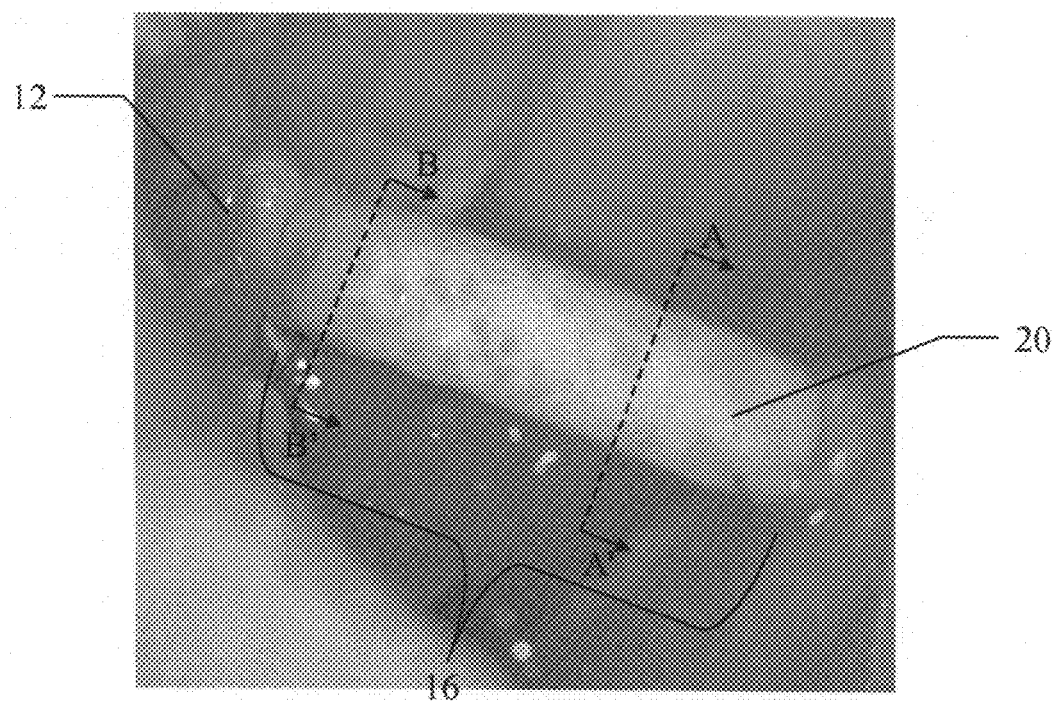

Referring to FIGS. 8a and 8b, adult Sprague Dawley rats 10 (200~250 g) were deeply anesthetized with chloral hydrate (400 mg/kg), and received a bilateral nerve crushing operation. Sciatic nerves 12 were exposed and cut off with a scissor to remove 8 mm of sciatic nerves 12. Due to the shrinkage of the nerve, the space between both sciatic nerve ends extended to 10 mm. Next, the implantable medical device 20 for nerve repair of the invention, with a length of 10 mm, was disposed between both sciatic nerve ends 16, and the remaining nerves received bilateral epineurial neurorrhaphy using 9-0 ETHILON sutures to fix in both sides of the implantable medical device 20. After recovery rom the anesthetic, animals were returned to standard housing.

One month (n=3) and three months (n=4) after surgery, animals were lavaged with 4% paraformaldehyde, and the implantable medical device 20 and regenerated nerve were removed, immersed in 5% glutaraldehyde and embedded in resin. Next, the embedded regenerated nerve was especially evident in semi-thin sections stained with toluidine blue. The toluidine blue stained nerve sections were placed on the stage of a microscope and viewed with phase optics.

Figure 9A:
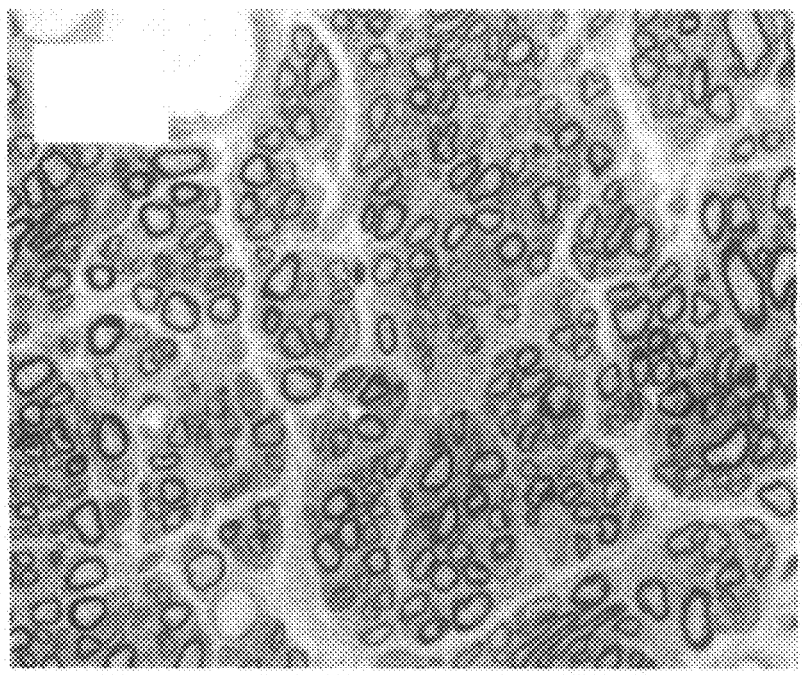
FIGS. 9a and 9b are SEM (Scanning Electron Microscope) spectrographs showing cross-sections along line A-A' and line B-B' of FIG. 8b.
Figure 9B:
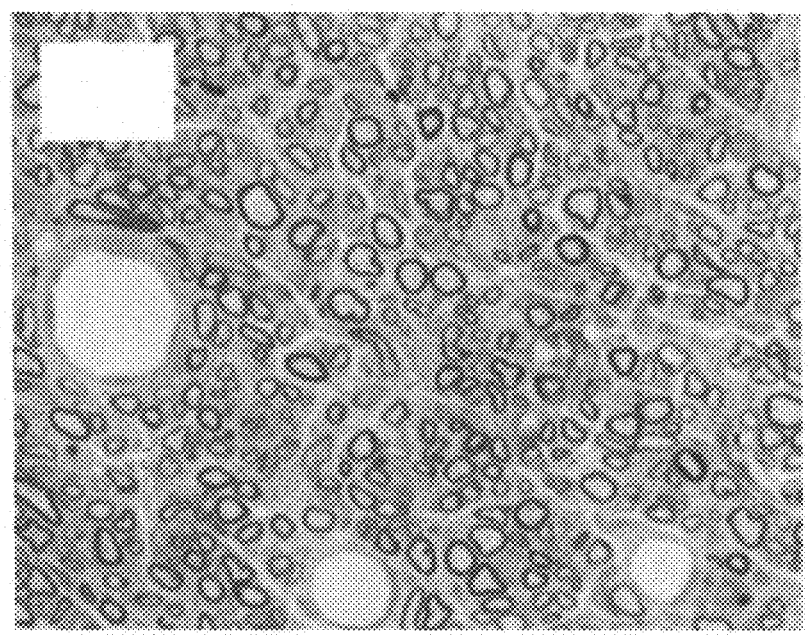

The regenerated nerve fibers were recognized inside hollow aliphatic polyester copolymer tube 20 by observing the cross-section of the tube 20. FIGS. 9a and 9b respectively show the cross-sections of the tube along line A-A' (one month after surgery) and line B-B' (three months after surgery) of FIG. 8b. The line A-A' is 3 mm apart from one end 16 of the tube 20, and the line B-B' is 10 mm apart from one end 16 of the tube 20. Accordingly, the sciatic nerves of the rat were repaired and regenerated. Regenerated nerve fibers could be recognized inside the porous hollow aliphatic polyester copolymer tube (Implant 3 months)

Preparation of Implantable Medical Device (Dura Substitute) for Dura Mater Repair Example 19

Figure 10A:
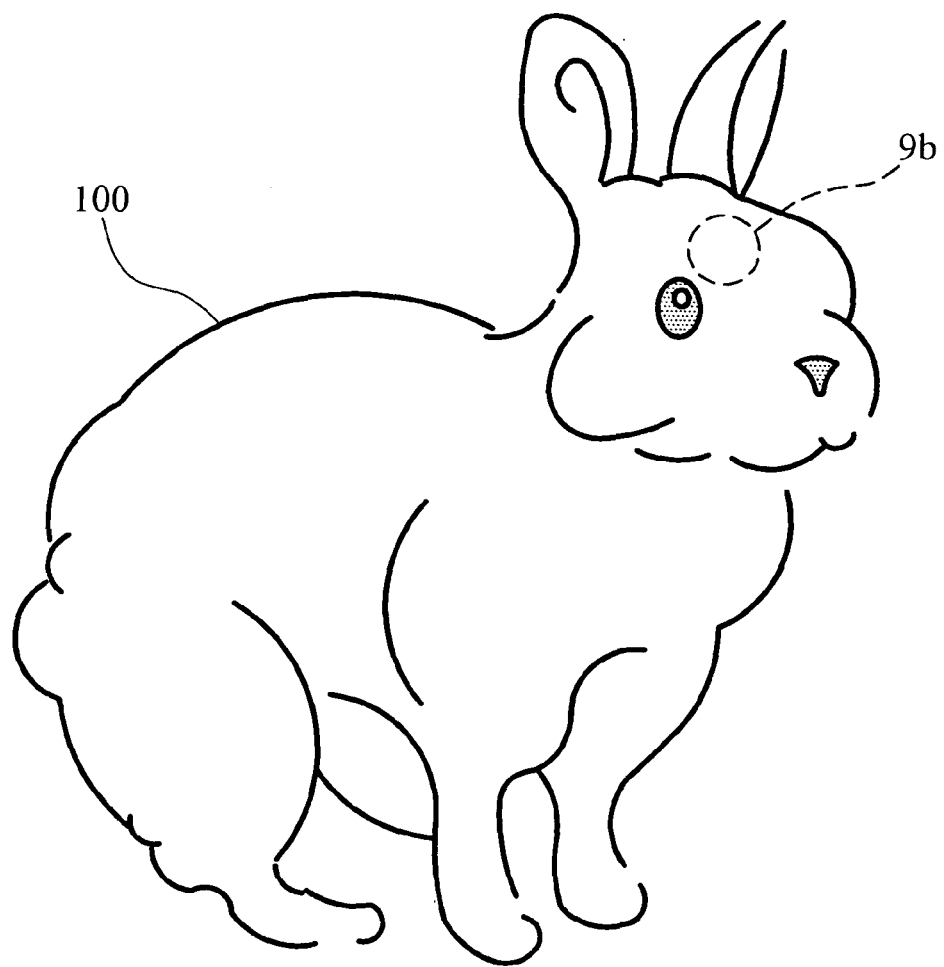
FIGS. 10a and 10b are schematic diagrams of rabbit dura mater repair of Example 19.
Figure 10B:
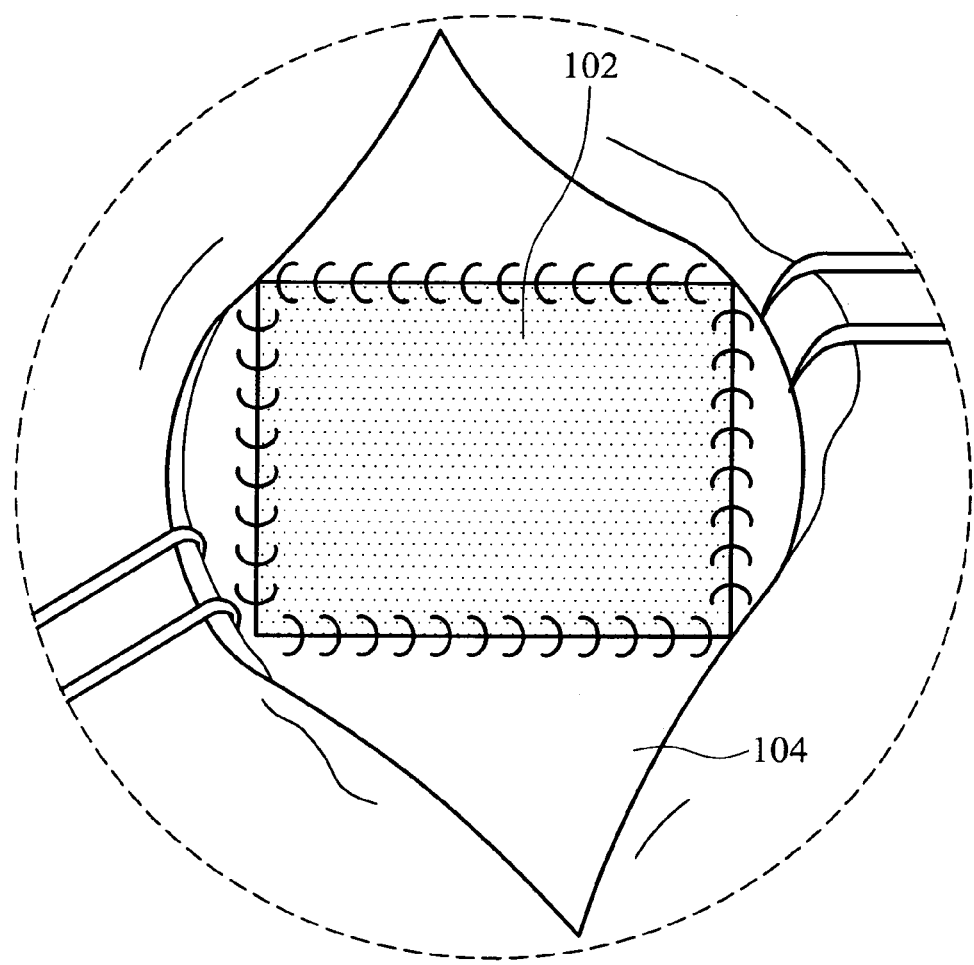

20 g of polyester of Example 5 and 20 g of polyethylene glycol with a molecular weight of 300 (PEG300) were dissolved in 60 g of DMAC. After stirring completely, the mixture was put into a sandblasted glass with a rough surface to fabricate a coating with a thickness of 1.4 mm. The coating was stood at 25±2° C. Next, the coating was immersed into a coagulator (water) at 25±2° C. for 4 hours, to form a porous polyester film. Next, the porous polyester film was immersed into a cleaning agent (40 wt % acetone) for 2 hours and then immersed into water for 6 hours, and dried The porous polyester film was used to form a rectangular dural substitute with a diameter of 15×12 mm. New Zealand White Rabbits (2-3 kg), employed for the evaluation of the efficacy of the dural substitute, were anesthetized with intramuscular injection of Ketamine hydrochloride (50 mg/Kg) and Xylazine (2%, 1 ml/Kg). Following a midline incision, bilateral frontoparietal craniotomy was performed. Referring to FIG. 10a, a 12×10 mm$^2$ piece of dura mater of the rabbit 100 was excised. Referring to FIG. 10b, in the treatment group, the rectangular dural substitute 102 with appropriate size was placed on the cortex and sutured to the edge of the dura mater 104 in a continuous fashion with No. 7-0 prolene monofilament. In the control group, the dura mater was opened and then sutured with No. 7-0 prolene monofilament, without using any dural substitute. The cranial bone flap was replaced and the pericranium and the skin were sutured with No. 4-0 nylon filament.

One month after surgery, the health of the subject was assessed, and no ill effect (excepting slight foreign body reaction) observed, indicating the dural substitute has superior bio-compatibility.

Figure 11A:
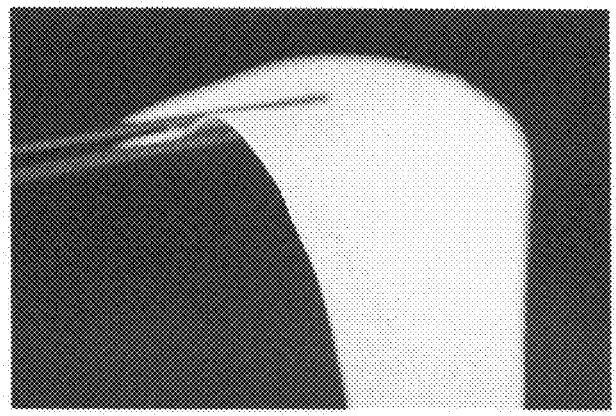
FIG. 11a is a photograph of the dural substitute used in Example 19.
Figure 11B:
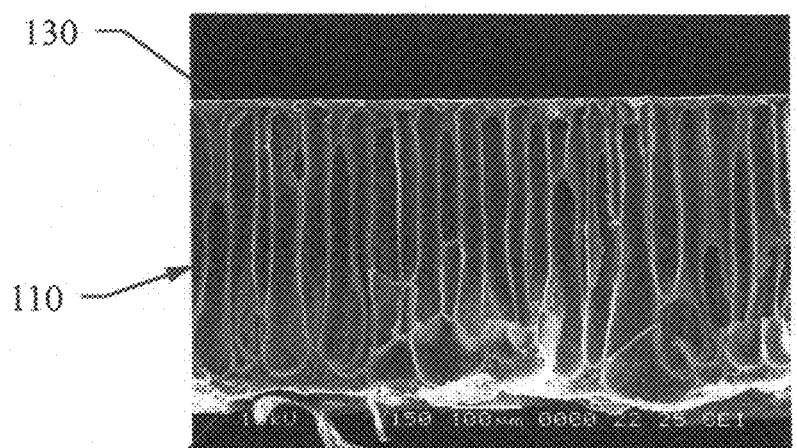
FIG. 11b is a SEM (Scanning Electron Microscope) spectrograph showing the cross-section of the dural substitute used in Example 19.
Figure 11C:
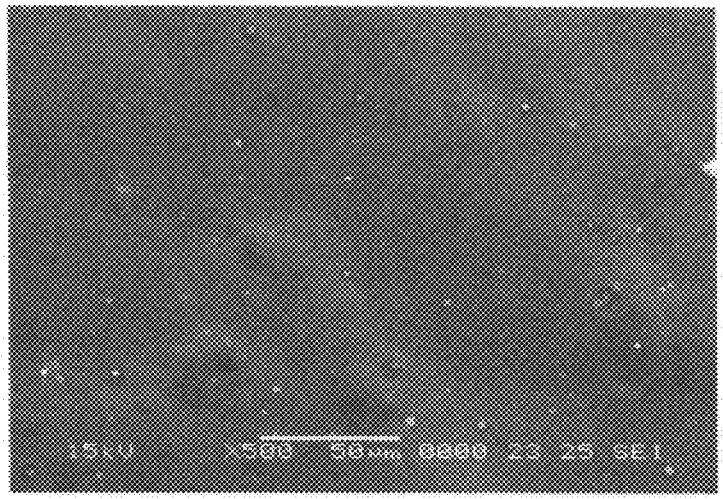
FIGS. 11c and 11d are SEM (Scanning Electron Microscope) spectrographs respectively showing the smooth surface and rough surface of the dural substitute used in Example 19.
Figure 11D:
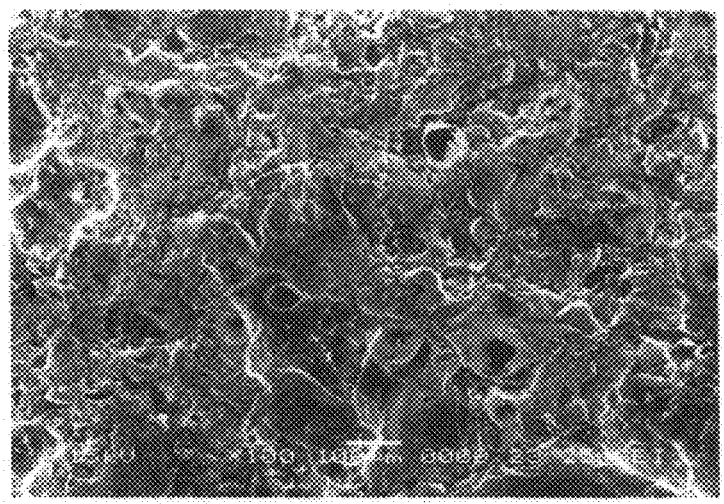
Figure 12A:
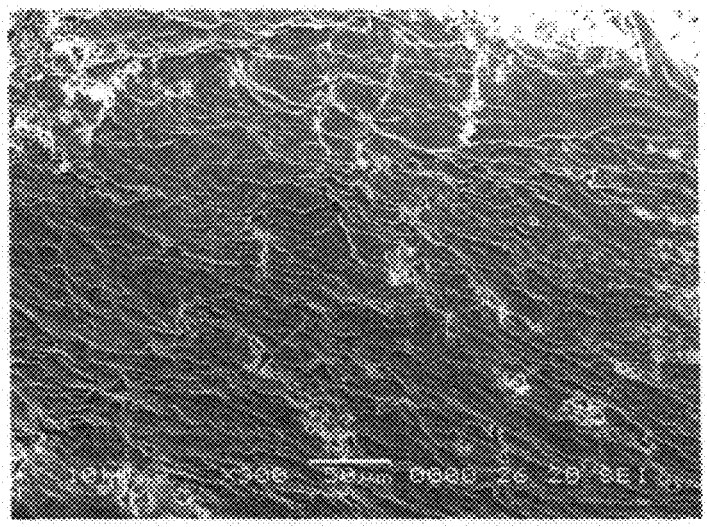
FIGS. 12a and 12b are SEM (Scanning Electron Microscope) spectrographs respectively showing the smooth surface and rough surface of the dural substitute one month after surgery.
Figure 12B:
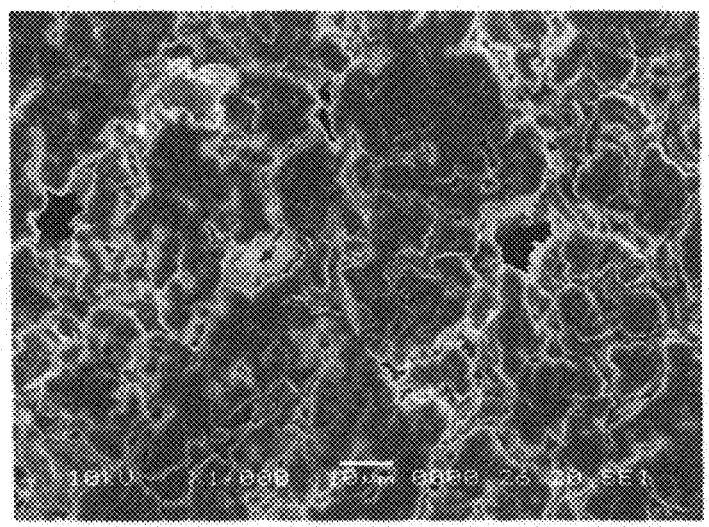
Figure 13:
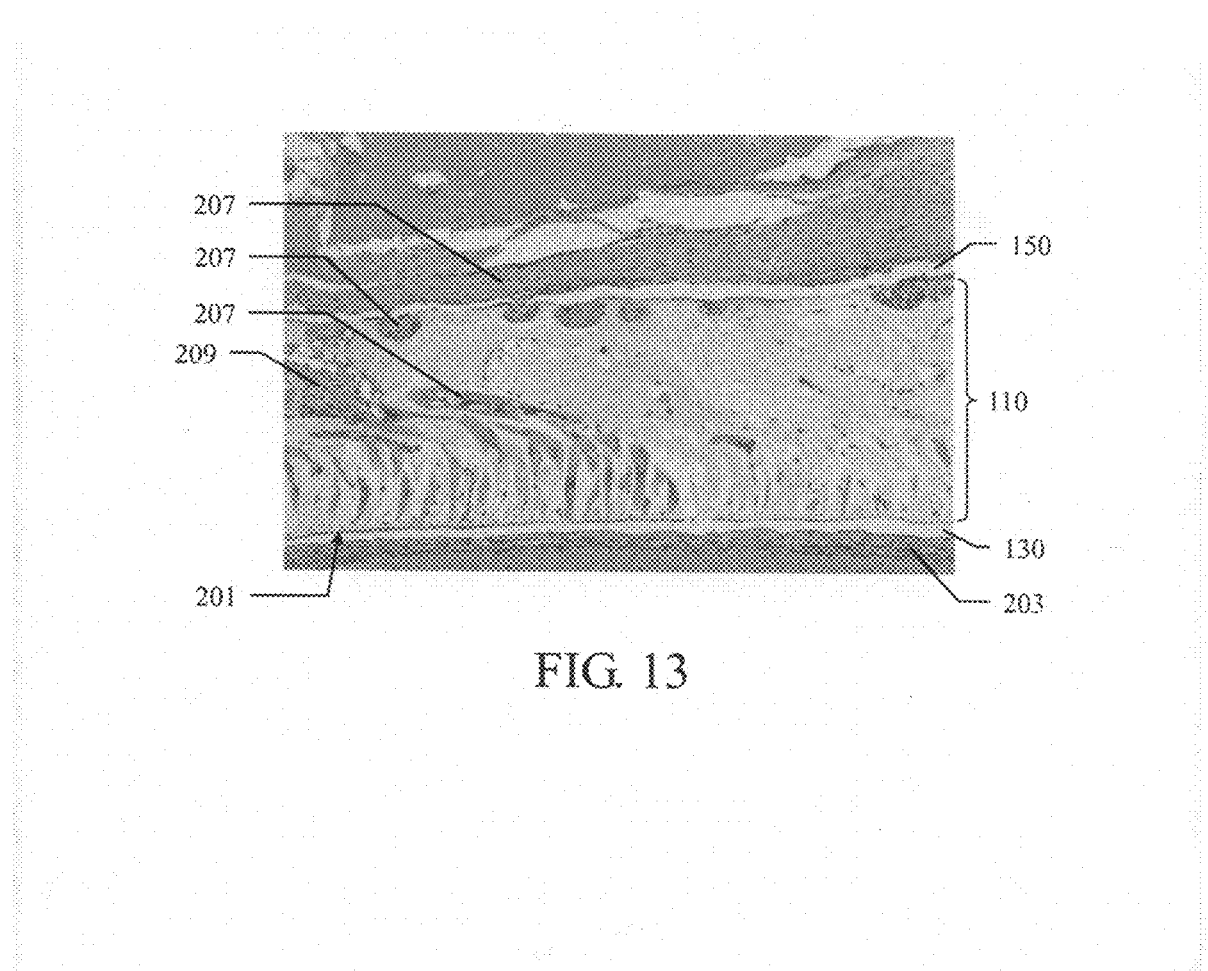
FIG. 13 shows the tissue section around the dural substitute one month after surgery

FIG. 11a is a photograph of the dural substitute 102 of Example 19, and FIG. 11b is a SEM (Scanning Electron Microscope) spectrograph showing a cross-section of the dural substitute 102. As shown in FIGS. 11b~11d, the dural substitute 102 has porous structure 110, a smooth surface 130 (referring to FIG. 11c), and a rough surface 150 (referring to FIG. 11d). FIGS. 12a and 12b respectively show the SEM (Scanning Electron Microscope) spectrograph of smooth surface 130 and a rough surface 150, and FIG. 13 shows the tissue section around the dural substitute 102, one month after surgery. Accordingly, mono-layer cells 201, formed between the surfaces 130 and 150 of the dural substitute 102 and the pia mater 203 of host are observed. Further, host tissues 207 and blood capillaries 209 are found inside the dural substitute 102. It means that the dura meter tissues of the host are repaired and regenerated. Moreover, the smooth surface 130 of the dural substitute 102 preventing dural substitute from tissue adhesion. As shown in FIG. 13, there is no tissue adhesion which was observed by tissue section spectrography.

As a main feature and a key aspect of the invention, referring to SEM spectrograph showing the morphology of the dural substitute, a plurality of cracks formed on the surface of the dural substitute were observed one month after surgery, resulting from degradation of aliphatic polyester copolymer. The weight of the dural substitute one month after surgery was measured at 5% less in comparison with the original dural substitute.

The rabbits of the control group and the treatment group were sacrificed after one and three months respectively.

As a main feature and a key aspect, the aliphatic polyester copolymer of the invention is prepared from at least two polyesters which have the same repeat units, but different weight average molecular weights. Thus, the biodegradation period of the aliphatic polyester copolymer can be optionally adjusted by modifying the difference of weight average molecular weights of polyesters, the weight ratio of polyesters, and the selection of coupling agent. Furthermore, the aforementioned variables also render the crystallinity of the aliphatic polyester copolymer, thereby increasing the variation of biodegradation.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An aliphatic polyester copolymer, the reaction product of reactants comprising:
   a first polyester;
   a second polyester; and
   a coupling agent,
   wherein the first polyester and second polyester have the same repeat units, but different weight average molecular weights, wherein the difference of the weight average molecular weights between the first polyester and the second polyester are of more than 200 daltons.

2. The aliphatic polyester copolymer as claimed in claim 1, wherein the repeat unit is derived from monomers of caprolactone, butyrolactone, D,L-lactide, D-lactide, L-lactide, D,L-lactide acid, D-lactide acid, L-lactide acid, glycolide, glycolic acid, hydroxy hexonoic acid, hydroxy butyric acid, valerolactone, hydroxy valeric acid, hydroxybutyric acids, malic acid, or copolymers thereof.

3. The aliphatic polyester copolymer as claimed in claim 1, wherein the repeat unit of polyester is derived from monomers of caprolactone, butyrolactone, L-lactide, D-lactide, D,L-lactide, L-lactic acid, D-lactic acid, D,L-lactic acid, glycolide, glycolic acid, or copolymers thereof.

4. The aliphatic polyester copolymer as claimed in claim 1, wherein the weight average molecular weights of the first and second polyesters are 150-50000 daltons.

5. The aliphatic polyester copolymer as claimed in claim 1, wherein the weight average molecular weights of the first and second polyesters are 200-30000 daltons.

6. The aliphatic polyester copolymer as claimed in claim 1, wherein the weight average molecular weights of the first and second polyesters are 200-15000 daltons.

7. The aliphatic polyester copolymer as claimed in claim 1, wherein the biodegradation period of the aliphatic polyester copolymer is adjustable.

8. The aliphatic polyester copolymer as claimed in claim 7, wherein the biodegradation period of the aliphatic polyester copolymer is adjusted by modifying the weight ratio between the first and second polyester.

9. The aliphatic polyester copolymer as claimed in claim 7, wherein the biodegradation period of the aliphatic polyester copolymer is adjustable by modifying the difference of the weight average molecular weights between the first polyester and the second polyester.

10. The aliphatic polyester copolymer as claimed in claim 1, wherein the difference of the weight average molecular weights between the first polyester and the second polyester are of more than 500 daltons.

11. The aliphatic polyester copolymer as claimed in claim 1, wherein the coupling agent comprises an agent of aliphatic isocyanate compounds having 2 or more —N=C=O groups and mixtures thereof.

12. The aliphatic polyester copolymer as claimed in claim 1, wherein the coupling agent comprises methylene-bis-(4-cyclohexyl diisocyanate) ($H_{12}MDI$), 1,6-Diisocyanatohexane (HDI), 5-Isocyanato-1-(isocyanatomethyl)-1,3,3-trimethylcyclohexane (IPDI), Tetramethyl-m-xylylene diisocyanate (TMXDI) or mixtures thereof.

13. The aliphatic polyester copolymer as claimed in claim 1, wherein the coupling agent is methylene-bis-(4-cyclohexyl diisocyanate) ($H_{12}MDI$).

14. The aliphatic polyester copolymer as claimed in claim 1, wherein the biodegradation period of the aliphatic polyester copolymer is 1~36 months.

15. The aliphatic polyester copolymer as claimed in claim 1, wherein the biodegradation period of the aliphatic polyester copolymer is of less than 36 months.

16. The aliphatic polyester copolymer as claimed in claim 1, wherein the biodegradation period of the aliphatic polyester copolymer is 13~36 months.

17. The aliphatic polyester copolymer as claimed in claim 1, wherein the biodegradation period of the aliphatic polyester copolymer is 1~12 months.

18. The aliphatic polyester copolymer as claimed in claim 1, wherein the reactants further comprise a catalyst.

19. The aliphatic polyester copolymer as claimed in claim 18, wherein the catalyst comprises organometallic catalyst, amine catalyst, or mixtures thereof.

20. The aliphatic polyester copolymer as claimed in claim 19, wherein the organometallic catalyst comprises dibutyltin dilaurate, tertbutyl titanate, dibutyltin, stannous octoate, or mixtures thereof.

21. The aliphatic polyester copolymer as claimed in claim 19, wherein the amine catalyst comprises N,N-Dimethylcyclohexylamine, 1,1,3,3-tetramethylguanidine, tetramethylethylenediaminoriethylene diamine, tripropylene glycol, N,N'-dimethylpiperazine, N,N,N',N'-tetramethyl-1,3-butanediamine, trimethylpiperazine, 1,4-bis(2-hydroxypropyl)-2-methylpiperazine, N-hydroxyethylpiperazine, 1,3,5-tris(dimethylaminopropyl)hexahydrostriazine, dimethylbenzylamine, 4-ethylmorpholine, 2,2-dimorpholinoethyl ether, triethylamine, 2,2'-bis(2-ethyl-2-azobicycloether), diazobicyclooctane, dimethylaminopropylamine, diethylaminoethylamine, or mixtures thereof.

22. A method for fabricating aliphatic polyester copolymer, comprising:
   reacting a first polyester, a second polyester, and a coupling agent undergoing copolymerization,
   wherein the first polyester and second polyester are prepared from the same oligomer or low molecular weight polymer, but have different weight average molecular weights, wherein the difference of the weight average molecular weights between the first polyester and the second polyester are of more than 200 daltons.

23. The method as claimed in claim 22, wherein the copolymerization is carried out in the form of a bulk polymerization, solution polymerization, emulsion polymerization, dispersion polymerization, suspension polymerization, or reactive extrusion.

24. The method as claimed in claim 22, wherein the copolymerization is carried out in the form of a bulk polymerization, solution polymerization, or reactive extrusion.

25. An implantable medical device, comprising the aliphatic polyester copolymer as claimed in claim 1.

26. The implantable medical device as claimed in claim 25, wherein the implantable device serves a medical device utilized in nerve repair, dura mater repair, ligament repair, tendon repair, hernia repair, rotator cuff repair, meniscal repair, muscle repair, joint repair, spinal repair, craniofacial repair, and maxiofacial repair, for repairing hard or soft tissues.

27. The implantable medical device as claimed in claim 25, wherein the implantable device serves a medical device utilized in nerve repair, spinal repair, and dura mater repair.

28. The implantable medical device as claimed in claim 25, wherein the implantable medical device is a tube, multi-channel tube, film, filmic curl, pin, plank, or sponge.

29. The implantable medical device as claimed in claim 26, wherein the implantable medical device has a solid or porous structure.

30. The implantable medical device as claimed in claim 25, wherein the implantable device is a dura mater substitute with multi-layer structure having a smooth surface preventing brain nerves from tissue adhesion with the dura mater substitute and having a rough surface facilitating the proliferation of dural tissue.

31. The implantable medical device as claimed in claim 30, wherein the dura mater substitute is a film with a thickness of 0.01~5 mm.

32. The implantable medical device as claimed in claim 30, wherein the peak-to valley height of the rough surfaces is between 10 μm to 1000 μm.

33. The implantable medical device as claimed in claim 25, wherein the implantable device is a nerve repair device.

34. The implantable medical device as claimed in claim 33, wherein the nerve repair device comprises a porous hollow tube.

35. The method as claimed in claim 22, wherein the copolymerization is carried out with a reaction temperature of 30° C.-200° C.

* * * * *

UNITED STATES PATENT AND TRADEMARK OFFICE
CERTIFICATE OF CORRECTION

| | | |
|---|---|---|
| PATENT NO. | : 7,902,303 B2 | Page 1 of 1 |
| APPLICATION NO. | : 11/606918 | |
| DATED | : March 8, 2011 | |
| INVENTOR(S) | : Yang et al. | |

It is certified that error appears in the above-identified patent and that said Letters Patent is hereby corrected as shown below:

ON THE TITLE PAGE:

Please insert the following:

Item -- Related U.S. Application Data

(60) Provisional application No. 60/754,641, filed on Dec. 30, 2005. --

Signed and Sealed this

Nineteenth Day of July, 2011

David J. Kappos
*Director of the United States Patent and Trademark Office*